(12) United States Patent
Kotra et al.

(10) Patent No.: US 10,143,706 B2
(45) Date of Patent: Dec. 4, 2018

(54) DECARBOXYLATED CANNABIS RESINS, USES THEREOF AND METHODS OF MAKING SAME

(71) Applicant: CannScience Innovations Inc., Toronto (CA)

(72) Inventors: Lakshmi Premakanth Kotra, Toronto (CA); Melissa Maureen Lewis, Brampton (CA); Ewa Wasilewski, Etobicoke (CA); Har Grover, Toronto (CA)

(73) Assignee: CannScience Innovations, Inc., Toronto (CA)

(*) Notice: Subject to any disclaimer, the term of this patent is extended or adjusted under 35 U.S.C. 154(b) by 0 days.

(21) Appl. No.: 15/637,043

(22) Filed: Jun. 29, 2017

(65) Prior Publication Data

US 2018/0000857 A1    Jan. 4, 2018

Related U.S. Application Data

(60) Provisional application No. 62/356,262, filed on Jun. 29, 2016.

(51) Int. Cl.
| | | |
|---|---|---|
| *A61K 36/00* | (2006.01) | |
| *A61K 31/775* | (2006.01) | |
| *A61K 31/352* | (2006.01) | |
| *G01N 30/02* | (2006.01) | |
| *A61K 36/185* | (2006.01) | |
| *A61P 25/00* | (2006.01) | |
| *A61P 29/00* | (2006.01) | |

(52) U.S. Cl.
CPC .......... *A61K 31/775* (2013.01); *A61K 31/352* (2013.01); *A61K 36/185* (2013.01); *A61P 25/00* (2018.01); *A61P 29/00* (2018.01); *G01N 30/02* (2013.01); *A61K 2236/00* (2013.01); *G01N 2030/027* (2013.01)

(58) Field of Classification Search
CPC .................................................... A61K 36/00
USPC ........................................................ 424/725
See application file for complete search history.

(56) References Cited

U.S. PATENT DOCUMENTS

| | | | |
|---|---|---|---|
| 4,221,778 A | 9/1980 | Raghunathan | |
| 4,279,824 A | 7/1981 | Mckinney | |
| 6,061,926 A | 5/2000 | Pare et al. | |
| 6,403,126 B1 | 6/2002 | Webster et al. | |
| 6,730,519 B2 | 5/2004 | Elsohly et al. | |
| 6,946,150 B2 | 9/2005 | Whittle | |
| 7,025,992 B2 | 4/2006 | Whittle et al. | |
| 7,344,736 B2 | 3/2008 | Whittle et al. | |
| 7,592,468 B2 | 9/2009 | Goodwin et al. | |
| 7,709,536 B2 | 5/2010 | Whittle | |
| 8,211,946 B2 | 7/2012 | Whittle | |
| 8,227,627 B2 | 7/2012 | Stinchcomb et al. | |
| 8,481,085 B2 | 7/2013 | Musty et al. | |
| 8,481,091 B2 | 7/2013 | Ross | |
| 8,512,767 B2 | 8/2013 | Ross | |
| 8,603,515 B2 | 12/2013 | Whittle | |
| 8,652,529 B2 | 2/2014 | Guimberteau et al. | |
| 8,673,368 B2 | 3/2014 | Guy et al. | |
| 8,742,305 B2 | 6/2014 | Simunovic et al. | |
| 8,895,063 B2 | 11/2014 | Guimberteau et al. | |
| 9,017,737 B2 | 4/2015 | Kikuchi et al. | |
| 9,023,400 B2 | 5/2015 | Guimberteau et al. | |
| 9,029,423 B2 | 5/2015 | Whittle | |
| 9,044,390 B1 | 6/2015 | Speier | |
| 9,186,386 B2 | 11/2015 | Speier | |
| 9,205,063 B2 | 12/2015 | Guy et al. | |
| 9,732,009 B2 | 8/2017 | Raber et al. | |
| 2003/0215496 A1 | 11/2003 | Patel et al. | |
| 2004/0192760 A1 | 9/2004 | Whittle et al. | |
| 2008/0167483 A1 | 7/2008 | Whittle et al. | |
| 2010/0249223 A1 | 9/2010 | Di Marzo et al. | |
| 2011/0098348 A1 | 4/2011 | De Meijer | |
| 2012/0046352 A1 | 2/2012 | Hospodor | |
| 2012/0245224 A1 | 9/2012 | Guy et al. | |
| 2013/0281324 A1 | 10/2013 | Gouliaev et al. | |
| 2013/0296398 A1 | 11/2013 | Whalley et al. | |
| 2013/0334045 A1 | 12/2013 | Kuhr et al. | |
| 2013/0337477 A1 | 12/2013 | Kuhr et al. | |
| 2013/0338234 A1 | 12/2013 | Splinter et al. | |
| 2014/0107192 A1 | 4/2014 | Maione et al. | |
| 2014/0155456 A9 | 6/2014 | Whalley et al. | |
| 2014/0228438 A1 | 8/2014 | Iuvone et al. | |

(Continued)

FOREIGN PATENT DOCUMENTS

| | | |
|---|---|---|
| CA | 2402020 A1 | 9/2001 |
| CA | 2438097 A1 | 8/2002 |

(Continued)

OTHER PUBLICATIONS

"Aseptiwave", "Aseptic", Industrial Microwave Tube exfoliated Furnace for graphite and graphene synthesis devices, Aseptia (2017); 3 pages, downloaded Jan. 12, 2017, http://aseptia.com/aseptiwave/.

(Continued)

*Primary Examiner* — Michael V Meller
(74) *Attorney, Agent, or Firm* — Cooley LLP

(57) ABSTRACT

The disclosure relates to decarboxylated *cannabis* resins and methods of making the decarboxylated *cannabis* resins by extraction and decarboxylation of cannabinoids from *Cannabis* species using microwaves and solvents. The disclosure also relates to use of the decarboxylated *cannabis* resins for making pharmaceutical products comprising same.

10 Claims, 31 Drawing Sheets

(56) References Cited

U.S. PATENT DOCUMENTS

| | | | |
|---|---|---|---|
| 2014/0243405 | A1 | 8/2014 | Whalley et al. |
| 2014/0271940 | A1 | 9/2014 | Wurzer et al. |
| 2014/0343136 | A1 | 11/2014 | Izzo et al. |
| 2014/0378539 | A9 | 12/2014 | Maione et al. |
| 2015/0148872 | A1 | 5/2015 | Martinez-orgado et al. |
| 2015/0203434 | A1 | 7/2015 | Flockhart et al. |
| 2016/0015683 | A1 | 1/2016 | Mccarty |
| 2016/0058866 | A1 | 3/2016 | Sekura et al. |
| 2016/0143972 | A1 | 5/2016 | Stebbins et al. |

FOREIGN PATENT DOCUMENTS

| | | | |
|---|---|---|---|
| CA | 2533400 | A1 | 8/2002 |
| CA | 2446195 | A1 | 11/2002 |
| CA | 2469490 | A1 | 7/2003 |
| CA | 2391454 | A1 | 12/2003 |
| CA | 2454644 | A1 | 2/2004 |
| CA | 2455129 | A1 | 2/2004 |
| CA | 2823474 | A1 | 2/2004 |
| CA | 2499210 | A1 | 4/2004 |
| CA | 2504802 | A1 | 5/2004 |
| CA | 2611760 | A1 | 12/2006 |
| CA | 2626074 | A1 | 5/2007 |
| CA | 2636634 | A1 | 7/2007 |
| CA | 2653835 | A1 | 12/2007 |
| CA | 2655094 | A1 | 12/2007 |
| CA | 2656698 | A1 | 12/2007 |
| CA | 2659162 | A1 | 2/2008 |
| CA | 2684562 | A1 | 10/2008 |
| CA | 2708921 | A1 | 7/2009 |
| CA | 2766082 | A1 | 1/2011 |
| CA | 2794620 | A1 | 10/2011 |
| CA | 2833099 | A1 | 11/2012 |
| CA | 2845677 | A1 | 4/2013 |
| CA | 2872528 | A1 | 11/2013 |
| CA | 2874968 | A1 | 12/2013 |
| CN | 100581586 | A | 1/2010 |
| CN | 102585999 | * | 7/2012 |
| CN | 103446100 | A | 12/2013 |
| EP | 1280515 | A2 | 2/2003 |
| EP | 1361864 | A2 | 11/2003 |
| EP | 1536810 | A2 | 6/2005 |
| EP | 1542657 | A1 | 6/2005 |
| EP | 1562581 | A2 | 8/2005 |
| EP | 1942880 | A1 | 7/2008 |
| EP | 1976506 | A1 | 10/2008 |
| EP | 2034987 | A1 | 3/2009 |
| EP | 2037901 | A1 | 3/2009 |
| EP | 2037902 | A1 | 3/2009 |
| EP | 2173332 | A1 | 4/2010 |
| EP | 2175848 | A1 | 4/2010 |
| EP | 2182940 | A1 | 5/2010 |
| EP | 2249848 | A1 | 11/2010 |
| EP | 2282630 | A2 | 2/2011 |
| EP | 2286793 | A2 | 2/2011 |
| EP | 2292211 | A2 | 3/2011 |
| EP | 2298283 | A2 | 3/2011 |
| EP | 2298284 | A2 | 3/2011 |
| EP | 2311475 | A2 | 4/2011 |
| EP | 2314284 | A2 | 4/2011 |
| EP | 2332533 | A1 | 6/2011 |
| EP | 2448637 | A1 | 5/2012 |
| EP | 2552430 | A1 | 2/2013 |
| EP | 2661263 | A1 | 11/2013 |
| EP | 2709604 | A1 | 3/2014 |
| EP | 2726069 | A1 | 5/2014 |
| EP | 2760440 | A1 | 8/2014 |
| EP | 2782563 | A1 | 10/2014 |
| EP | 2858633 | A1 | 4/2015 |
| GB | 2381194 | A | 4/2003 |
| GB | 2391865 | A | 2/2004 |
| GB | 2392093 | A | 2/2004 |
| GB | 2394894 | A | 5/2004 |
| GB | 2434312 | A | 7/2007 |
| GB | 2438682 | A | 12/2007 |
| GB | 2450493 | A | 12/2008 |
| GB | 2450741 | A | 1/2009 |
| GB | 2450753 | A | 1/2009 |
| GB | 2451254 | A | 1/2009 |
| GB | 2456183 | A | 7/2009 |
| GB | 2471523 | A | 1/2011 |
| GB | 2479153 | A | 1/2011 |
| GB | 2487712 | A | 8/2012 |
| GB | 2491118 | A | 11/2012 |
| GB | 2492487 | A | 1/2013 |
| GB | 2495118 | A | 4/2013 |
| GB | 2504263 | A | 1/2014 |
| GB | 2513167 | A | 10/2014 |
| KR | 100274734 | B1 | 12/2000 |
| WO | WO 1993/009785 | A1 | 5/1993 |
| WO | WO 2001/037808 | A1 | 5/2001 |
| WO | WO 2001/066089 | A2 | 9/2001 |
| WO | WO 2002/064109 | A3 | 8/2002 |
| WO | WO 2003/061563 | A2 | 7/2003 |
| WO | WO 2003/064407 | A2 | 8/2003 |
| WO | WO 2004/016246 | A1 | 2/2004 |
| WO | WO 2004/016277 | A2 | 2/2004 |
| WO | WO 2004/026802 | A1 | 4/2004 |
| WO | WO 2004/026857 | A2 | 4/2004 |
| WO | WO 2004/041269 | A2 | 5/2004 |
| WO | WO 2004/067004 | A1 | 8/2004 |
| WO | WO 2006/053329 | A2 | 5/2006 |
| WO | WO 2006/124676 | A1 | 11/2006 |
| WO | WO 2006/133733 | A1 | 12/2006 |
| WO | WO 2006/134018 | A2 | 12/2006 |
| WO | WO 2007/052013 | A1 | 5/2007 |
| WO | WO 2007/054378 | A1 | 5/2007 |
| WO | WO 2007/083098 | A1 | 7/2007 |
| WO | WO 2007/135193 | A2 | 11/2007 |
| WO | WO 2007/138322 | A1 | 12/2007 |
| WO | WO 2007/144628 | A1 | 12/2007 |
| WO | WO 2007/148094 | A1 | 12/2007 |
| WO | WO 2008/017752 | A2 | 2/2008 |
| WO | WO 2008/024408 | A2 | 2/2008 |
| WO | WO 2008/024490 | A2 | 2/2008 |
| WO | WO 2008/027442 | A2 | 3/2008 |
| WO | WO 2008/129258 | A1 | 10/2008 |
| WO | WO 2008/136636 | A1 | 11/2008 |
| WO | WO 2009/001081 | A1 | 12/2008 |
| WO | WO 2009/004302 | A1 | 1/2009 |
| WO | WO 2009/007697 | A1 | 1/2009 |
| WO | WO 2009/013506 | A1 | 1/2009 |
| WO | WO 2009/073633 | A1 | 6/2009 |
| WO | WO 2009/087351 | A1 | 7/2009 |
| WO | WO 2009/125198 | A2 | 10/2009 |
| WO | WO 2010/150245 | A1 | 12/2010 |
| WO | WO 2011/001169 | A1 | 1/2011 |
| WO | WO 2011/121351 | A1 | 10/2011 |
| WO | WO 2011/127933 | A1 | 10/2011 |
| WO | WO 2012/093255 | A1 | 7/2012 |
| WO | WO 2012160358 | A1 | 11/2012 |
| WO | WO 2013/005017 | A1 | 1/2013 |
| WO | WO 2013/045891 | A1 | 4/2013 |
| WO | WO 2013/076487 | A1 | 5/2013 |
| WO | WO 2013/182862 | A1 | 12/2013 |
| WO | WO 2014/036954 | A1 | 3/2014 |
| WO | WO 2014/159688 | A1 | 10/2014 |
| WO | WO 2014/170649 | A1 | 10/2014 |
| WO | WO 2015/069763 | A2 | 5/2015 |
| WO | WO 2015/070167 | A1 | 5/2015 |
| WO | WO 2015/140736 | A1 | 9/2015 |
| WO | WO 2016/004410 | A1 | 1/2016 |
| WO | WO 2016/014454 | A1 | 1/2016 |
| WO | WO 2016/084075 | A1 | 6/2016 |
| WO | WO 2016/092539 | A1 | 6/2016 |
| WO | WO 2017/053731 | A1 | 3/2017 |
| WO | WO 2018/000094 | A1 | 1/2018 |

OTHER PUBLICATIONS

"Continuous Microwave Cylindrical Heating System", IMS brochure (2008), IMS, L.L.C., 4 pages, downloaded May 10, 2018, http://www.google.com/url?sa=t&rct=j&q=&esrc=s&source=web

(56) References Cited

OTHER PUBLICATIONS

&cd=1&ved=0ahUKEwi38ZeCu_zaAhWnxlQKHZNIBYsQFg-gnMAA&url=http%3A%2F%2Fwww.industrialmicrowave.com%2Fpdf%2Fims_100_kw_chs_brochure.pdf&usg=AOvVaw0_fC8UkttRDdfCCaMAwfd.

"Cylindrical Heating Systems (CHS)", Industrial Microwave Systems, Inc., Product Information, 8 pages, downloaded Jan. 12, 2017, http://www.industrialmicrowave.com/productsCylindrical.htm.

"Industrial Microwave Technology Inches Toward Mainstream", Food Processing (2015); 7 pages, downloaded Jan. 12, 2017, https://www.foodprocessing.com/articles/2015/industrial-microwave-technology/?start=1, Aseptia-Aseptiwave.

"Remington: The Science and Practice of Pharmacy, 22nd Edition." Reviewed by Sheila Hayes, Edited by Aloyd V. Allen, Jr., J Med Libr Assoc. (2014); 102 (3): 220-221, 2 pages.

"Research and Bespoke Equipment", Product Summary, Food Processing—The Information for Food and Beverage Manufacturers, Industrial Microwave Systems Ltd. (2015); 2 pages, downloaded Jan. 12, 2017, http://www.industrial-microwave-systems.com/index_files/page847.htm.

"Buprenorphine Sublingual Tablets", (0.4 mg, 2 mg, 8 mg), PL 00240/0347, PL 00240/0354 and PL 00240/0355, Medicines and Healtcare Products Regulatory Agency (MHRA), Patient Information and Packaging, 46 pages. downloaded May 10, 2018, www.mhra.gov.uk/home/groups/par/documents/websiteresources/con096936.pdf.

"Subutex 2mg sublingual tablets", Summary of Product Characteristics, 10 pages, downloaded Dec. 5, 2016, https://www.medicines.org.uk/emc/print%ADdocument?documentId=26461.

Abruzzo, A., et al., "Mucoadhesive chitosan/gelatin films for buccal delivery of propranolol hydrochloride." Carbohydrate Polymers (2012); 87 (1): 581-588 (Abstract).

Al-Khattawi, A., et al., "Evidence-Based Nanoscopic and Molecular Framework for Excipient Functionality in Compressed Orally Disintegrating Tablets." PLoS One (2014); 9(7): e101369.

Al-Nimry, S.S., et al., "Development and evaluation of a novel dosage form of diltiazem HCl using ethylene vinyl acetate copolymer and sodium starch glycolate (in vitro/in vivo study)." J. Appl. Polym. Sci. (2012); pp. 1-12.

Ameur, et al., "Cloud point extraction of Δ9—tetrahydrocannabinol from cannabis resin." Analytical and Bioanalytical Chemistry (2013); 405: 3117-3123.

Bayrak, Z., et al., "Formulation of zolmitriptan sublingual tablets prepared by direct compression with different polymers: In vitro and in vivo evaluation." European Journal of Pharmaceutics and Biopharmaceutics (2011); 78 (3): 499-505.

Bolourchian, N., et al., "Development and optimization of a sublingual tablet formulation for physostigmine salicylate." Acta Pharm. (2009); 59(3): 301-312.

Cardelle-Cobas, A., et al., "Development of Oral Strips Containing Chitosan as Active Ingredient: A Product for Buccal Health." International Journal of Polymeric Materials and Polymeric Biomaterials (2015); 64 (17): 906-918 (Abstract).

Continuous flow reactors, SAIREM (2015); 1 page, downloaded Jan. 12, 2017, http://www.sairem.com/continuous-flow-reactors-61.html.

DeBruyne, D., et al., "Identification and differentiation of resinous cannabis and textile cannabis: combined use of HPLC and high-resolution GLC." Bull Narc. (1981); 33 (2): 49-58.

Decarboxylation: How much heat and time?, International Cannagraphic (2014); 12 pages, downloaded May 3, 2018, https://www.icmag.com/ic/showthread.php?t=295473.

Desai, P.M., et al., "Functionality of Disintegrants and Their Mixtures in Enabling Fast Disintegration of Tablets by a Quality by Design Approach." AAPS PharmSciTech. (2014); 15 (5): 1093-1104.

Drug Delivery—Films, Strips & diskettes, PharmaQuesT, 29 pages, downloaded May 11, 2018, "http://pharmaquest.weebly.com/uploads/9/9/4/2/9942916/films_strips_diskettes. pdf".

El-Setouhy, et al., "Bioenhanced sublingual tablet of drug with limited permeability using novel surfactant binder and microencapsulated polysorbate: In vitro/in vivo evaluation." Eur J Pharm Biopharm. (2015); 94: 386-392.

Fouad, S.A., et al., "Novel instantly-soluble transmucosal matrix (ISTM) using dual mechanism solubilizer for sublingual and nasal delivery of dapoxetine hydrochloride: In-vitro/in-vivo evaluation." International Journal of Pharmaceutics (2016); 505: 212-222.

Giri and SA, "Preparation and Evaluation of Rapidly Disintegrating Fast Release Tablet of Diazepam-Hydroxypropyl-β-Cyclodextrin Inclusion Complex." Pharmacology & Pharmacy (2010); 1: 18-26.

Gohel, M.C., et al., "Preparation and Assessment of Novel Coprocessed Superdisintegrant Consisting of Crospovidone and Sodium Starch Glycolate: A Technical Note." AAPS PharmSciTech (2007); 8 (1) Article 9, E1-E7.

How exactly do I microwave and decarboxylate cannabis?, 2017, 4 pages, downloaded May 3, 2018, https://www.quora.com/How-exactly-do-I-microwave-and-decarboxylate-cannabis.

Jelvehgari, et al., "Fast Dissolving Oral Thin Film Drug Delivery Systems Consist of Ergotamine Tartrate and Caffeine Anhydrous." Pharmaceutical Sciences (2015); 21: 102-110.

Kasperek, R., et al., "Release Kinetics of Papaverine Hydrochloride from Tablets with Different Excipients." Sci Pharm. (2014); 82: 683-696.

Khoo, C.G., et al., "Oral gingival delivery systems from chitosan blends with hydrophilic polymers." Eur J Pharm Biopharm. (2003); 55 (1): 47-56 (Abstract).

Latif, R., "Zero-order release profile of metoclopramide hydrochloride sublingual tablet formulation." Pharmaceutical Development and Technology (2013); 18 (6): 1372-1378.

Lee, D., et al., "Can oral fluid cannabinoid testing monitor medication compliance and/or cannabis smoking during oral THC and oromucosal Sativex administration?" Drug Alcohol Depend. (2013); 130 (0): 68-76.

LFPH9020 Industrial Microwave Tube exfoliated Furnace for graphite and graphene synthesis devices, Changsha Langfeng Microwave Technology Co., Ltd. (2015); 9 pages, downloaded Jan. 12, 2017, http://www.industrialmicrowavefurnace.com/product/LF-PH9020-Industrial-Microwave-Tube-exfoliated-Furnace-for-graphite-and-graphene-synthesis-devices.html.

Microwave reactors at production scale, Feb. 11, 2010, Jayne E. Muir, Cambrex, 6 pages, downloaded Jan. 12, 2017, https://www.manufacturingchemist.com/technical/article_page/Microwave_reactors_at_production_scale/43817.

Morschhäuser, R., et al., "Microwave-assisted continuous flow synthesis on industrial scale." Green Process Synth (2012); 1: 281-290.

Niesink, R.J., et al., "Potency trends of Δ9-tetrahydrocannabinol, cannabidiol and cannabinol in cannabis in the Netherlands: 2005-15." Addiction (2015); 110 (12): 1941-1950 (Abstract).

Ofem, O.W., et al., "Some physical properties of novel Cannabis suppositories formulated with theobroma oil." African Journal of Pharmacy and Pharmacology (2014); 8 (44): 1127-1131.

Omar, J., et al., "Optimisation and characterisation of marihuana extracts obtained by supercritical fluid extraction and focused ultrasound extraction and retention time locking GC-MS." J Sep Sci. (2013); 36 (8): 1397-1404 (Abstract).

Pathare, Y.S., et al., "Polymers used for Fast Disintegrating Oral Films: A Review." Int. J. Pharm. Sci. Rev. Res. (2013); 21 (1) (No. 29): 169-178.

Prajapati, S., et al., "Formulation and evaluation of sublingual tablet containing Sumatriptan succinate." Int J Pharm Investig. (2012); 2 (3): 162-168.

Ruchlemer, R., et al., "Inhaled medicinal cannabis and the immunocompromised patient." Support Care Cancer (2015); 23 (3): 819-822 (Abstract).

Sayeed and Ashraf, "Considerations in Developing Sublingual Tablets—An Overview." Pharmaceutical Technology (2014); vol. 83, Issue 11, 9 pages. downloaded Dec. 5, 2016, http://www.pharmtech.com/print/262556?page=full.

(56) References Cited

OTHER PUBLICATIONS

Suprapaneni, M.S., et al., "Effect of excipient and processing variables on adhesive properties and release profile of pentoxifylline from mucoadhesive tablets." Drug Dev Ind Pharm. (2006); 32 (3): 377-387 (Abstract).
Tayel, A., et al., "Formulation of Ketotifen Fumarate Fast-Melt Granulation Sublingual Tablet.", AAPS PharmSciTech (2010); 11 (2): 679-685.
The Science of Cannabis—Extraction Methods & More, Mar. 24, 2017, by Rachel Wellendorf, 15 pages, downloaded May 3, 2018, http://greendreamcannabis.com/blog/the-science-of-cannabis#.
Varshosaz, J., et al., "Formulation, optimization and in vitro evaluation of rapid disintegrating and mucoadhesive sublingual tablets of Lorazepam." Farmacia (2015); 63 (2): 234-246.
Zamengo, et al., "Variability of cannabis potency in the Venice area (Italy): a survey over the period of 2010-2012." Drug Testing and Analysis (2014); 6 (1-2): 46-51.
International Search Report and Written Opinion for International Application No. PCT/CA2017/050788, dated Sep. 21, 2017, 13 pages.

* cited by examiner

Flow charts of various extractions methods
Figure 29A Ultrasonic Extraction
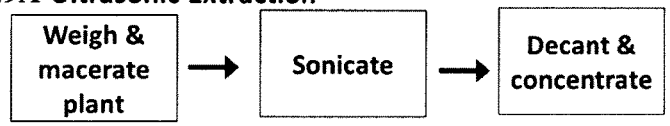
Figure 29B Soxhlet Extraction
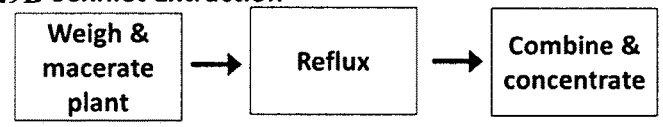
Figure 29C Supercritical Fluid Extraction (SFE)
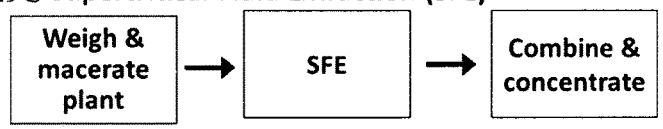
Figure 29D Closed System Extraction (CSE)
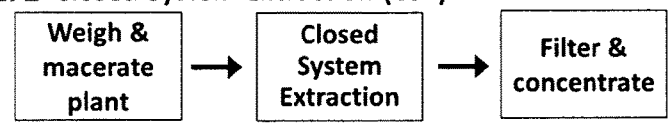
Figure 29A-D

DECARBOXYLATED CANNABIS RESINS, USES THEREOF AND METHODS OF MAKING SAME

CROSS REFERENCE TO PRIOR APPLICATIONS

This application claims priority under the Paris Convention to U.S. Provisional Patent Application Ser. No. 62/356,262, filed Jun. 29, 2016, which is incorporated herein by reference as if set forth in its entirety.

FIELD OF THE DISCLOSURE

The present disclosure relates to decarboxylated *cannabis* resins and use of the decarboxylated resins directly as medicines or natural health products, or as raw materials for making *cannabis*-derived products, including pharmaceutical products, pharmaceutical formulations and natural health products. The disclosure also relates to products and compositions comprising the decarboxylated *cannabis* resins. Also disclosed are methods of making the decarboxylated *cannabis* resins using microwave extraction and decarboxylation.

BACKGROUND OF THE DISCLOSURE

*Cannabis* is a genus of flowering plants in the family Cannabaceae. Three species may be recognized (*Cannabis sativa, Cannabis indica* and *Cannabis ruderalis*). *Cannabis* spp. contains a highly complex mixture of compounds, up to 568 unique molecules identified to date (Pertwee, R. G. e., *Handbook of cannabis*. Oxford University Press: Oxford, 2014). Cannabinoids are the most noteworthy compounds found in *Cannabis* spp. Among these compounds, $\Delta^9$-tetrahydrocannabinol ($\Delta^9$-THC), cannabinol (CBN), and cannabinodiol (CBDL) are known to be psychoactive (Pertwee, R. G. e., *Handbook of cannabis*. Oxford University Press: Oxford, 2014). Other cannabinoids such as cannabidiol (CBD), which is a non-psychoactive compound, exert their physiological effects through a variety of receptors including adrenergic and cannabinoid receptors (Pertwee, R. G. e., *Handbook of cannabis*. Oxford University Press: Oxford, 2014). Cannabinoid receptors (CB1 and CB2) belong to G-protein coupled receptors (GPCRs) (Cottone, E.; Pomatto, V.; Cerri, F.; Campantico, E.; Mackie, K.; Delpero, M.; Guastalla, A.; Dati, C.; Bovolin, P.; Franzoni, M. F. Cannabinoid receptors are widely expressed in goldfish: molecular cloning of a CB2-like receptor and evaluation of CB1 and CB2 mRNA expression profiles in different organs. Fish Physiology and Biochemistry 2013, 39 (5), 1287-1296). Phytocannabinoids produced by *Cannabis* spp. plants as well as endocannabinoids produced in our body bind to these receptors. Patients consume medical *cannabis* for the treatment of or seek relief from a variety of clinical conditions including pain, anxiety, epileptic seizures, nausea, and appetite stimulation (Galal, A. M.; Slade, D.; Gul, W.; El-Alfy, A. T.; Ferreira, D.; Elsohly, M. A. Naturally occurring and related synthetic cannabinoids and their potential therapeutic applications. Recent patents on CNS drug discovery 2009, 4 (2), 112 and Downer, E. J.; Campbell, V. A. Phytocannabinoids, CNS cells and development: A dead issue? Phytocannabinoids have neurotoxic properties. Drug and Alcohol Review 2010, 29 (1), 91-98). It is also known that cannabinoids and endocannabinoids affect the development and maturation of neural cells in early life (Downer, E. J.; Campbell, V. A. Phytocannabinoids, CNS cells and development: A dead issue? Phytocannabinoids have neurotoxic properties. Drug and Alcohol Review 2010, 29 (1), 91-98). Cannabinoid-like compounds isolated from flax have also shown anti-inflammatory properties (Styrczewska, M.; Kulma, A.; Ratajczak, K.; Amarowicz, R.; Szopa, J. Cannabinoid-like anti-inflammatory compounds from flax fiber. *Cellular & Molecular Biology Letters* 2012, 17 (3), 479-499).

Most cannabinoids are concentrated in a viscous resin produced in structures of the *cannabis* plant known as glandular trichomes. At least 113 different cannabinoids have been isolated from the *cannabis* plant, the most common being $\Delta^9$-tetrahydrocannabinolic acid ($\Delta^9$-THC-A) which is the non-active precursor of the psychoactive $\Delta^9$-tetrahydrocannabinol ($\Delta^9$-THC).

$\Delta^9$-THC-A is found in variable quantities in fresh, undried *cannabis*, but is progressively decarboxylated to $\Delta^9$-THC with drying, and especially under intense heating such as when *cannabis* is smoked or cooked into *cannabis* edibles.

$\Delta^9$-THC is not the only substance obtained from *cannabis* with therapeutic benefits to people. For example, studies have shown that cannabidiol (CBD), another major constituent of some strains of *cannabis*, has been found to be anxiolytic and to have antipsychotic properties, and may be neuroprotective in humans.

FIG. 1A shows chemical structures of six major cannabinoids present in or which can be obtained from *cannabis*: $\Delta^9$-THC, $\Delta^9$-THC-A, $\Delta^8$-THC, cannabinol (CBN), $\Delta^2$-CBD and cannabidiolic acid ($\Delta^2$-CBD-A). FIG. 1B shows the cannabinolic acid synthase pathway of cannabigerolic acid (CBGA) to cannabidiolic acid (CBDA), tetrahydrocannabinolic acid (THCA) and cannabichromenic acid (CBCA), which can all be decarboxylated to active cannabinoid forms. In some cases, the non-decarboxylated cannabinoids may also have therapeutic properties.

Decarboxylation is a chemical reaction that releases carbon dioxide and generates neutral cannabinoids. In one example in *cannabis*, the non-psychoactive $\Delta^9$-THC-A can be converted to psychoactive $\Delta^9$-THC by decarboxylation.

There is a need to produce a *cannabis* resin comprising cannabinoids that are decarboxylated. The *cannabis* resins or extracts known in the art may not be consistently and fully decarboxylated and comprise significant proportions of THCA and CBDA. For example, see WO 2014/159688. The *cannabis* extracts or resins of the art are for use, for example, in vaporization, infusion into edible matrices, and inhalation via electronic inhalation devices. Accordingly, the extracts and resins of the art comprise predominantly THCA and/or CBDA, as opposed to their decarboxylated counterparts (THC and CBD respectively), and it is only after heating the extracts and resins via vaporization or cooking in edible matrices that decarboxylation occurs (i.e. only after heating the extracts and resins that the cannabinoids are decarboxylated into their active forms). As the *cannabis* resins of the present disclosure comprise decarboxylated therapeutically active cannabinoids, they may be used directly. For example, the *cannabis* resins of the present disclosure may be used directly in therapy or used to develop various *cannabis* formulations for pharmaceutical products that do not need to be further heated (i.e. decarboxylated) into therapeutically active forms.

Many people may be reluctant to use *cannabis* (either as a medicine or natural health product) if it has to be "smoked" or heated (i.e. "vaping"). This may be because there are negative perceptions to smoking and vaping, especially in the older generation. Many people may be more accepting of *cannabis* if it is in a form that is more conventional (i.e.

tablet form, or other conventional forms of medicine). In order, to produce conventional forms of *cannabis* for use as a medicine or natural health product, the cannabinoids in the product must be decarboxylated.

There is also a need to develop an efficient method of extracting and decarboxylating cannabinoids from *cannabis*.

To date the simplest mechanism to perform decarboxylation of cannabinoid acids is by heating. Other processes of decarboxylation require toxic solvents. In these systems, a distillation process such as fractional distillation may be employed to separate the organic solvents from the *cannabis* extract after decarboxylation.

In addition to decarboxylation, extraction of cannabinoids from the plant material is required. Extraction is most often done prior to decarboxylation. Mechanisms of extraction of cannabinoids such as $\Delta^9$-THCA and CBDA from *cannabis* that are known include sonication, reflux (Soxhlet) extraction and supercritical fluid extraction (SFE). For example, U.S. Pat. No. 9,044,390 describes a fractional SFE process of contacting *cannabis* plant material with a supercritical fluid solvent system at a pressure between about 750 psi and 25,000 psi, and at a temperature between about −15° C. and 200° C.

With the rise in the authorized use of *cannabis* for medical, therapeutic and recreational purposes, there is an increasing need for a reproducible method for obtaining a consistent active cannabinoid-comprising resin with known efficacy and to optimize production and recovery of active decarboxylated cannabinoids. With increasing demand and potential uses, there is also a need for a method that can be easily scaled-up for manufacture of commercial pharmaceutical preparations, natural health product preparations or recreational use preparations.

SUMMARY OF THE DISCLOSURE

The present disclosure provides a decarboxylated *cannabis* resin. The decarboxylated *cannabis* resin comprises the cannabinoid profile of the plant from which the resin was extracted, but the cannabinoids are decarboxylated. The cannabinoids are at least 90%-100% decarboxylated (i.e. 90%, 91%, 92%, 93%, 94%, 95%, 96%, 97%, 98%, 99% or 100%, or any fraction thereof, e.g. 93.3% decarboxylated). Unlike some of the *cannabis* resins of the prior art, the decarboxylated *cannabis* resin of the present disclosure can be used directly, for example, in therapy or can be used as a raw material to develop various pharmaceutical formulations that do not need to undergo heating for decarboxylation into therapeutically active forms.

In addition to the above decarboxylated cannabinoids, other chemicals found in *Cannabis* spp. and soluble in the solvent used, are found in the resin. Such compounds may include, for example, terpenes, fatty acids, chlorophyll, flavonoids, and other compounds. Some of the compounds may undergo chemical transformation due to the processes used for extraction and decarboxylation. In some embodiments, THC and/or CBD are the major components of the decarboxylated *cannabis* resin.

The present disclosure also provides an improved method of extracting and decarboxylating cannabinoids from *cannabis* plant material, the method comprising decarboxylating *cannabis* plant material before, during or after extraction using microwave technology.

In some embodiments the method comprises: chopping down or grinding down the *cannabis* plant material into smaller pieces to form *cannabis* plant material of a size and form suitable for extraction; extracting cannabinoids from the broken down *cannabis* plant material by contacting the broken down *cannabis* plant material with a solvent in a mixture to extract cannabinoids from the *cannabis* plant material and decarboxylating the cannabinoids in the mixture by subjecting the mixture to microwaves to form decarboxylated cannabinoids.

In some embodiments, the extraction and decarboxylation steps are done in one step, by exposing the plant material to a suitable solvent, (e.g. pharmaceutically acceptable solvent, for instance a solvent selected from the group of solvents consisting of: 80-100% ethanol (for example, 80%, 85%, 90%, 95%, 97%, 98%, 100%, and any integer or fraction of the integer thereof), ethylene glycol, isopropanol or a combination of similar solvents, and subjecting the plant material in the solvent to microwaves sufficient to obtain the desired decarboxylated cannabinoid comprising resin. If 100% decarboxylation is not required, the duration of the microwaving step can be adjusted to obtain the desired degree of decarboxylated cannabinoids in the resin. In some embodiments, the plant material in the solvent is placed in a microwave. In some embodiments it is subjected to microwaves for a time and/or at a pressure and/or at a temperature sufficient to produce desired decarboxylated (biologically active) cannabinoid comprising resin. In some embodiments, the chopping down, extraction and decarboxylation are done in one step.

In some embodiments when the extraction and decarboxylation steps are done in one step, the broken down *cannabis* plant material is suspended (for example, by stirring, shaking or agitation) in a solvent and subjected to microwaves resulting in an extracted and decarboxylated *cannabis* resin.

An embodiment of the disclosure is a decarboxylated *cannabis* resin, wherein the resin comprises decarboxylated cannabinoids from a *Cannabis* spp. plant, such that Δ9-tetrahydrocannabinolic acid (Δ9-THCA) and cannabidiolic acid (CBDA) cannabinoids in the plant are each independently 90% to 100% decarboxylated to yield Δ9-tetrahydrocannabinol (THC) and cannabidiol (CBD) respectively in the resin. The range of 90% to 100% decarboxylation includes any integer or fraction of an integer in this range, for example 90%, 88.4%, and 100%. The decarboxylated *cannabis* resin may further comprise cannabinol (CBN), other decarboxylated cannabinoids, or any compounds (for example, terpenes, chlorophyll), including for example, the compounds found on Table 32.

The decarboxylated *cannabis* resin may comprise less than 5% solvent by weight or by volume, or it may be is substantially free of solvent.

An embodiment of the disclosure is a pharmaceutical composition comprising (i) the decarboxylated *cannabis* resin of the disclosure and (ii) a suitable pharmaceutically acceptable carrier or excipient.

Another embodiment of the disclosure is a natural health product comprising the decarboxylated *cannabis* resin of the disclosure.

Another embodiment of the disclosure is a method of extracting and decarboxylating cannabinoids from plant material, the method comprising: (i) extracting cannabinoids from the *Cannabis* plant material by contacting the *Cannabis* plant material with a solvent to extract cannabinoids from the *Cannabis* plant material, the extract of *Cannabis* comprising the solvent and cannabinoids; and (ii) decarboxylating the cannabinoids in (a) the plant material and (b) the extract comprising cannabinoids by subjecting the plant material and extract to microwaves at temperature of about 100-200° C. in a sealed container and for a time period sufficient to form the corresponding decarboxylated cannabinoids in the extract. The temperature may be any integer or fraction of an integer in the range of 100-200° C., for example 103° C., 175.5° C., and 200° C.

In some embodiments, the plant material is broken down to form *cannabis* plant material of a size and form suitable for extraction before the extracting step.

In some embodiments, the extracting and decarboxylating occur concurrently.

In some embodiments, the *cannabis* plant material is suspended in the solvent by stirring or agitation.

In some embodiments, the solvent is selected from the group of solvents consisting of: 80-100% ethanol, ethylene glycol, isopropanol, and a combination of any of the above. The ratio of solvent to *cannabis* plant material may be such that the *Cannabis* plant material is submerged in the solvent in the sealed container.

In some embodiments, the time period is about 15-75 minutes depending on scale of the reaction.

In some embodiments, the temperature is about 130° C. to about 180° C., or about 150° C. to about 170° C.

In some embodiments, the microwaves have a frequency of about 2.45 GHz and a wavelength of about $1.22 \times 10^8$ nm.

In some embodiments, subjecting the plant material and extract to microwaves in the sealed container occurs under pressure of about 1-22 bar. The pressure may be any integer or fraction of an integer in the range of 1-22 bar, for example 1 bar, 15.5 bar and 18 bar.

In some embodiments the extracted and decarboxylated cannabinoids are recovered in the form of a *cannabis* resin or in the form of isolated compounds. For example, the decarboxylated cannabinoids may be recovered from the *cannabis* resin by separating (i) a single cannabinoid, (ii) a mixture of cannabinoids, (iii) a single compound or (iv) a mixture of compounds from the resin. The decarboxylated cannabinoids may be recovered using a Celite® and/or an activated charcoal carbon filter.

In some embodiments, the decarboxylated cannabinoids in the resin may be subjected to winterization for the removal of waxes.

In some embodiments, the *cannabis* plant material is dried prior to the breaking down step. In some embodiments, the *cannabis* plant material is dried *cannabis*.

In some embodiments, a further step of removing the solvent from the resin to obtain a substantially solvent-free decarboxylated *cannabis* resin is used.

In some embodiments, the *cannabis* plant material is trichomes, *cannabis* female inflorescence, flower bract, *cannabis* stalk, *cannabis* leaves, or combinations thereof.

In some embodiments, the solvent is removed from the resin.

An embodiment of the disclosure is the method of the disclosure done on a commercial scale.

An embodiment of the invention is the use of the *cannabis* resin of the disclosure in a natural health product or in a pharmaceutical product.

Additional aspects of the present application will be apparent in view of the description which follows. It should be understood, however, that the detailed description and the specific examples, while indicating embodiments of the disclosure, are given by way of illustration only, since various changes and modifications within the spirit and scope of the disclosure will become apparent to those skilled in the art from this detailed description.

Abbreviations:
Δ9-THC=Δ9-Tetrahydrocannabinol, CBD=Cannabidiol, CBN=Cannabinol, CBDL=Cannabinodiol, CBC=Cannabichromene, CBL=Cannabicyclol, CBE=Cannabielsoin, CBG=Cannabigerol, THV=Tetrahydrocannabivarin, CBDV=Cannabidivarin, CBCV=Cannabichromevarin, THCA=Tetrahydrocannabinolic acid, CBDA=Cannabidiolic acid, CBNA=Cannabinolic acid, CBCA=Cannabichromenic acid, CBLA=Cannabicyclolic acid, CBEA=Cannabielsoic acid, CBGA=Cannabigerolic acid, THCVA=Tetrahydrocannabivarinic acid, C1-THCRA=Tetrahydrocannabiorcolic acid, C4-THCA=C4-Tetrahydrocannabinolic acid, CBND=Cannabinodiol.

BRIEF DESCRIPTION OF THE DRAWINGS

In order that the subject matter may be readily understood, embodiments are illustrated by way of examples in the accompanying drawings, in which:

FIG. 29A Ultrasonication; FIG. 29B Sohxlet extraction; FIG. 29C Supercritical Fluid Extraction (Omar, J. Olivares, M. et al. J. Sep. Sci. 2013, 36, 1397-1404, incorporated herein by reference); FIG. 29D Closed system microwave extraction (in ethanol, hexane or isopropanol or liquid $CO_2$), as described in experiments 5-9 below.

DETAILED DESCRIPTION

As previously described, tetrahydrocannabinol (THC), or more precisely its main isomer $\Delta^9$-THC, is the principal psychoactive constituent (or cannabinoid) of *cannabis*. Unlike THC, its corresponding acid THC-A (or $\Delta^9$-THC-A for its main isomer) is a non-psychoactive cannabinoid found in raw and live *cannabis*.

$\Delta^9$-THC is only one of the family of compounds known as cannabinoids. For example, $\Delta^8$-THC is a double bond isomer of $\Delta^9$-THC and is a minor constituent of most varieties of *cannabis*. The major chemical difference between the two compounds is that $\Delta^9$-THC is easily oxidized to cannabinol (CBN) whereas $\Delta^8$-THC does not oxidize to cannabinol as it is very stable. $\Delta^8$-THC, for the most part, produces similar psychometric effects as does $\Delta^9$-THC, but is generally considered to be 50% less potent than $\Delta^9$-THC. On the other hand, CBD has no or limited psychometric activity on its own when administered to humans, however as discussed below CBD comprises other therapeutic qualities. In the *cannabis* plant, CBGA is a precursor and cannabinol (CBN), a metabolite of THC. As *cannabis* matures, THC gradually breaks down to CBN which also has psychoactive properties.

Figure 1A:
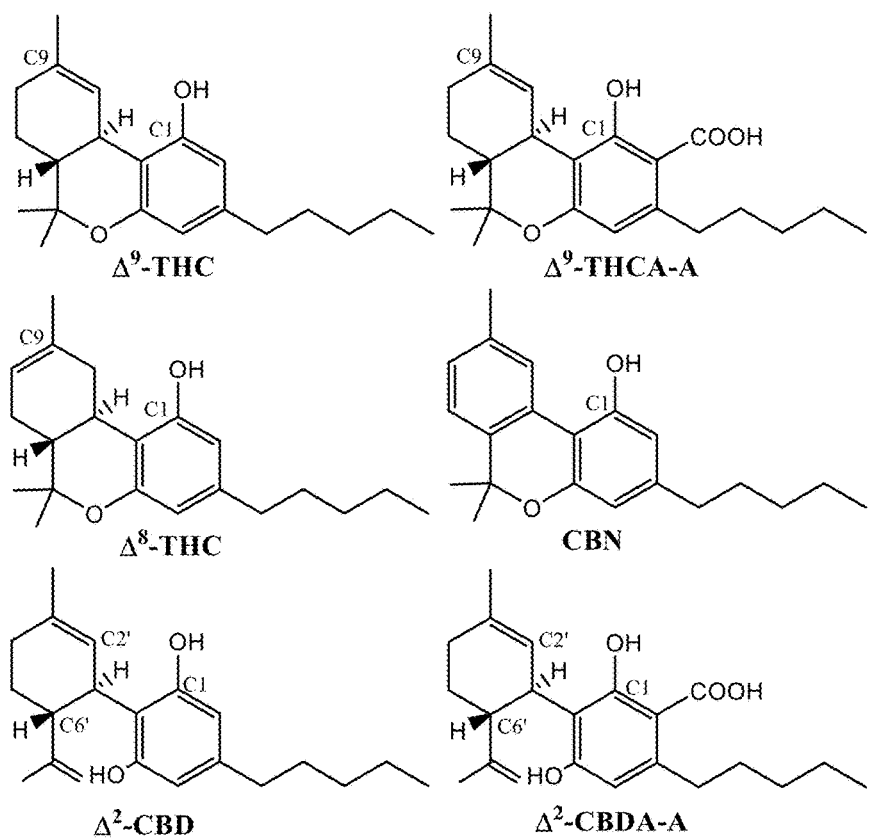
FIG. 1A shows chemical structures of six major cannabinoids present in *cannabis*: $\Delta^9$-THC, $\Delta^9$-THC-A, $\Delta^8$-THC, CBN, $\Delta^2$-CBD and $\Delta^2$-CBD-A.
Figure 1B:
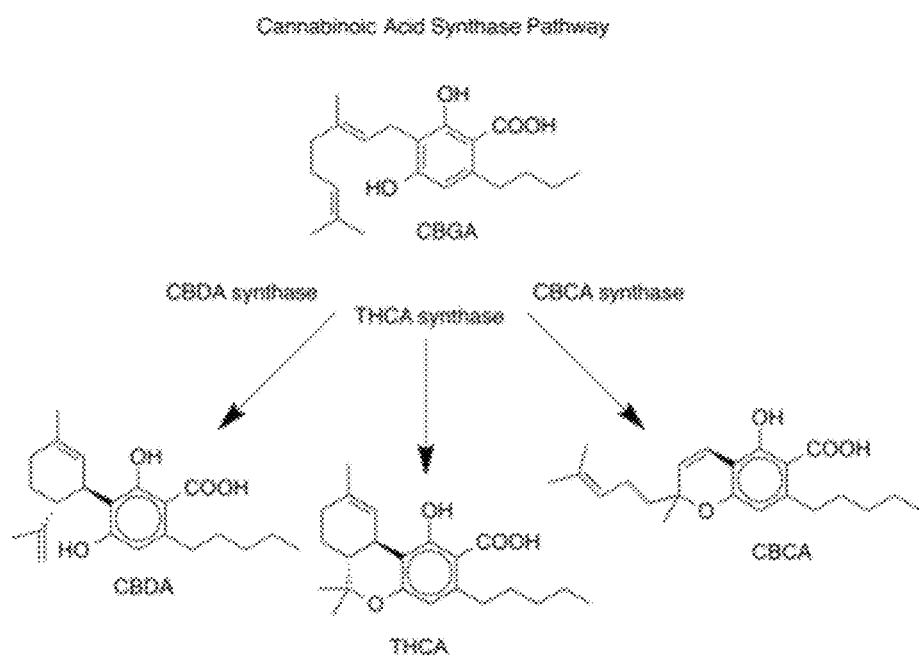
FIG. 1B shows the cannabinoic acid synthase pathway of cannabigerolic acid (CBGA) to cannabidiolic acid (CBDA), tetrahydrocannabinolic acid (THCA) and cannabichromenic acid (CBCA)

FIG. 1 shows the chemical structures of six major cannabinoids present in *cannabis*: $\Delta^9$-THC, $\Delta^9$-THC-A, $\Delta^8$-THC, CBN, $\Delta^2$-cannabidiol ($\Delta^2$-CBD or CBD) and $\Delta^2$-cannabidiolic acid ($\Delta^2$-CBD-A or CBD-A).

Figure 2A:
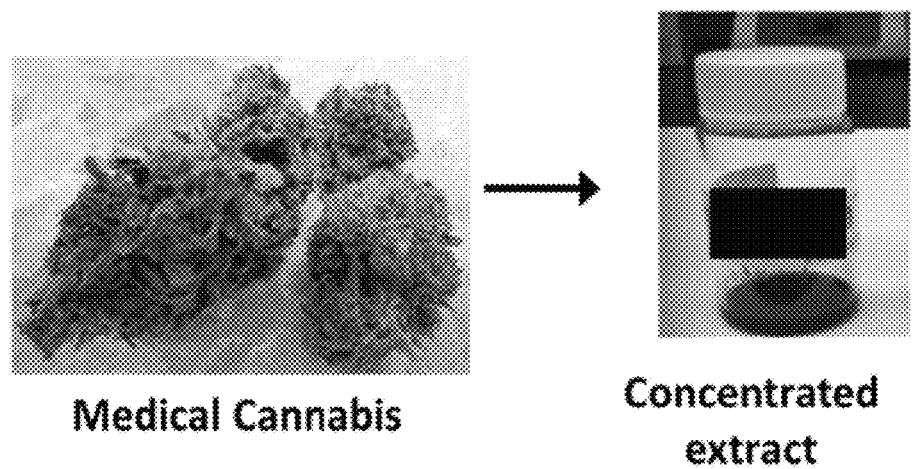
FIG. 2A shows medical *cannabis* and decarboxylated *cannabis* resin
Figure 2B:
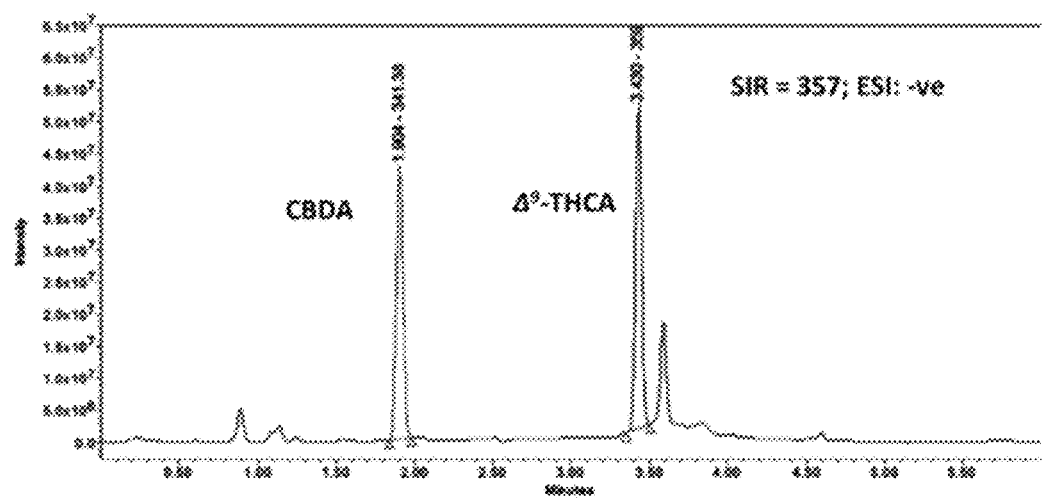
FIG. 2B is a mass spectra of Strain 1 before decarboxylation of medical *cannabis*
Figure 2C:
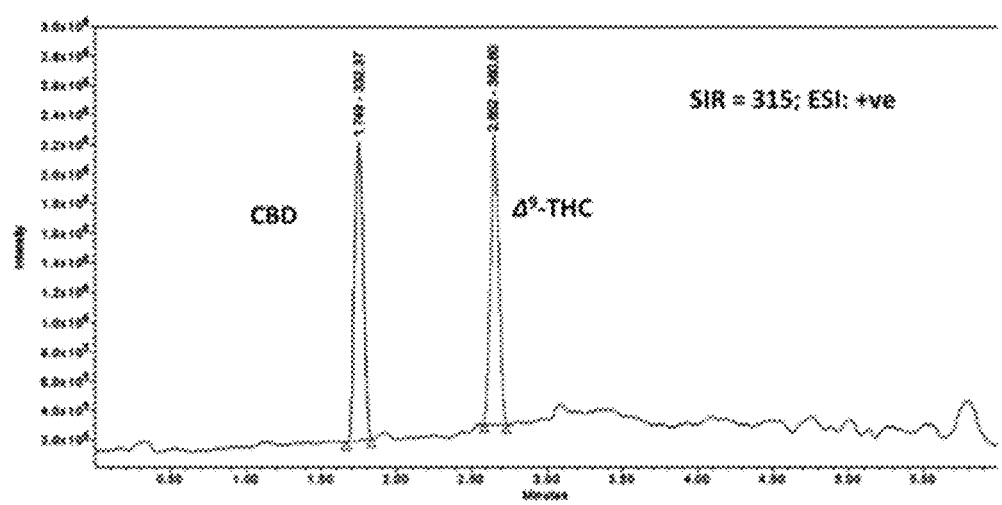
FIG. 2C is a mass spectra of Strain 1 after decarboxylation of medical *cannabis*

FIGS. 2a, 2b and 2c show the decarbosylated *cannabis* resin and the mass spectra of Strain 1 before (b) and after (c) decarboxylation of medical *cannabis*, and indicates 100% conversion of CBDA and THCA into CBD and THC, respectively.

Figure 3:
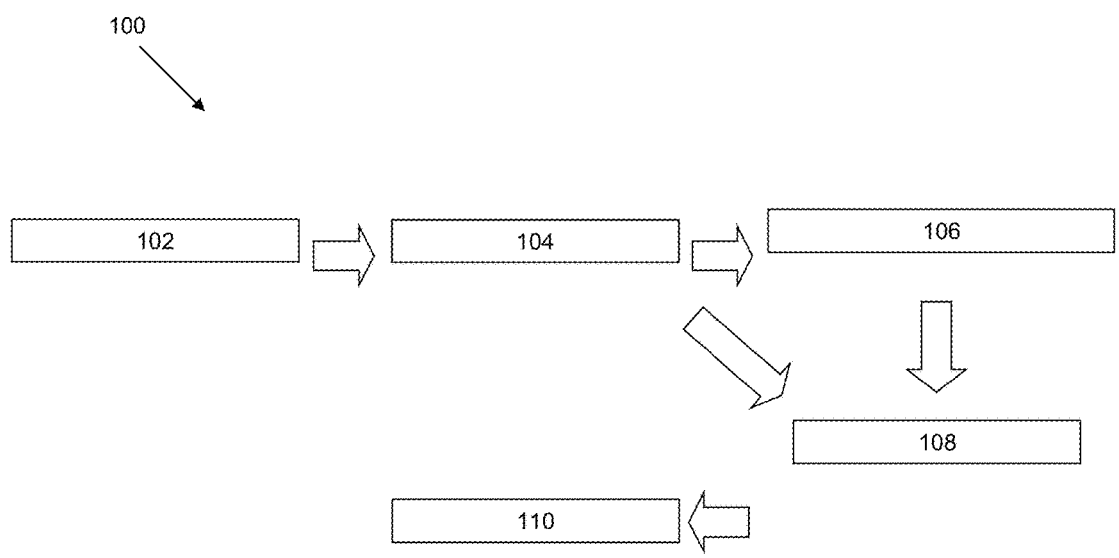
FIG. 3 is a block diagram illustrating a process for extracting and decarboxylating cannabinoids from *cannabis* plant material according to one embodiment of the application.

Turning to FIG. 3, a method 100 for extracting and decarboxylating cannabinoids from *cannabis* plant material is shown. Generally, method 100 comprises drying raw *cannabis* plant material at step 102, breaking down the *cannabis* plant material to form *cannabis* plant material of a size and form suitable for extraction at step 104, extracting cannabinoids from the broken down *cannabis* plant material by contacting the broken down *cannabis* plant material with a solvent to extract the cannabinoids from the *cannabis* plant material and decarboxylating the cannabinoids by subjecting the extract to microwaves to form decarboxylated cannabinoids. Decarboxylation of the cannabinoids may occur when the cannabinoids are in the plant, when the cannabinoids are in the extract, or both. In some embodiments the extract is subjected to microwaves in a closed reaction vessel at a temperature and time sufficient to form decarboxylated cannabinoid.

The extracted and decarboxylated cannabinoids are optionally recovered. Recovery can include filtering the solvent from the extract of *cannabis* plant material to isolate the decarboxylated cannabinoids.

In some embodiments, the process comprises an extraction step before, during or after decarboxylation. In some embodiments, the process of the disclosure comprises more than one extraction step.

In some embodiments, the decarboxylation step can occur before, during or after extraction.

In an embodiment of the disclosure, a one-step method for extraction and decarboxylation is used, wherein the *cannabis* plant material (that is suitably prepared, e.g. optionally dried and broken down as described herein) is placed in a suitable extracting solvent (e.g. a pharmaceutically acceptable solvent such as ethanol, glycerol, and isopropanol, and other solvents as is known to those skilled in the art, kept in suspension or solution (e.g. by stirring, agitation, shaking or other means known to those skilled in the art) and subjected to microwave radiation while stirring at a temperature, pressure and time to obtain suitably extracted and decarboxylated cannabinoids that can be recovered for use as either a mixture or individual chemical components (e.g. for use as a therapeutic or pharmaceutical product). Further in some embodiments, the solvent can be food grade oil and/or a medium chain triglyceride, for example, coconut oil.

Such a method is more efficient in converting the cannabinoid acid into its decarboxylated form than other known methods of extraction and decarboxylation (such as simple heating).

Figure 11:
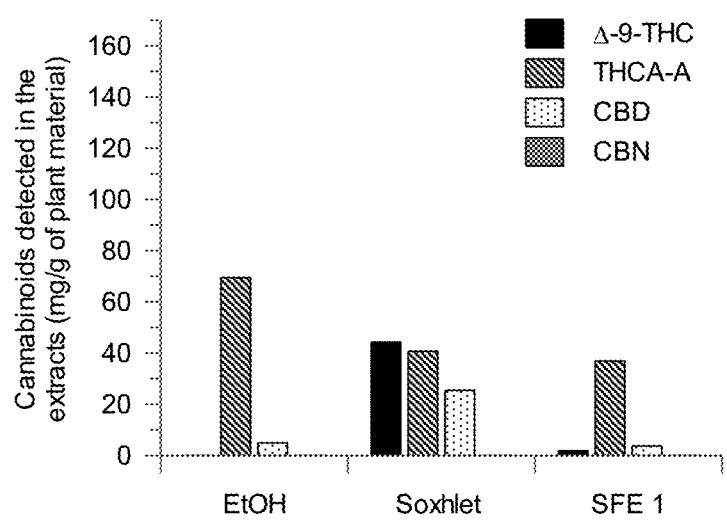
FIG. 11 shows concentrations of various cannabinoids in the *cannabis* extracts using ethanol, Soxhlet and SFE, without subjecting *cannabis* to microwave conditions.
Figure 12:
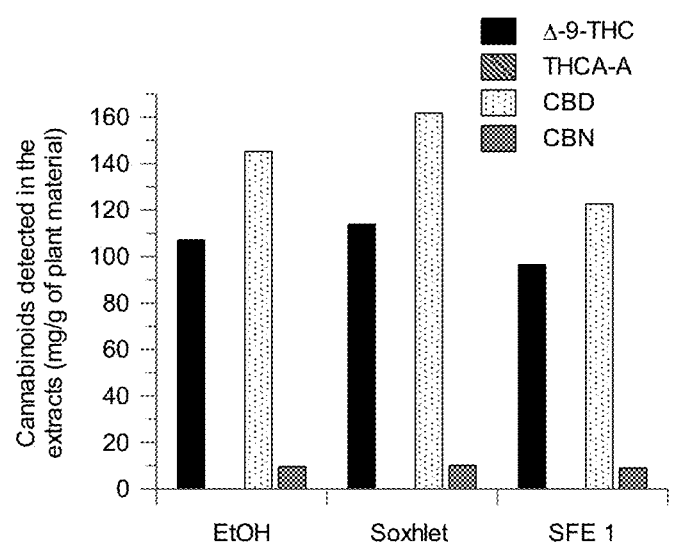
FIG. 12 shows concentrations of various cannabinoids in the *cannabis* extracts using ethanol, Soxhlet and SFE followed by microwave heating.

Particularly, FIGS. 11 and 12 show various concentrations of different cannabinoids in *cannabis* plant material extracts using ethanol, Soxhlet and SFE, without subjecting *cannabis* to microwave conditions and followed by microwave heating, respectively. By comparing concentrations measured through the use of solvent extraction alone, Soxhlet extraction alone (e.g. solvent and heat) and SFE alone (e.g. solvent and heat), as shown in FIG. 11, with concentrations measured by using solvent extraction followed by microwave, Soxhlet extraction followed by microwave and SFE followed by microwave, as shown in FIG. 12, adding microwave heating to each of solvent extraction, Soxhlet extraction and SFE can greatly increase THC, CBD and CBN concentrations and decrease THCA concentration in the extract.

Figure 13:
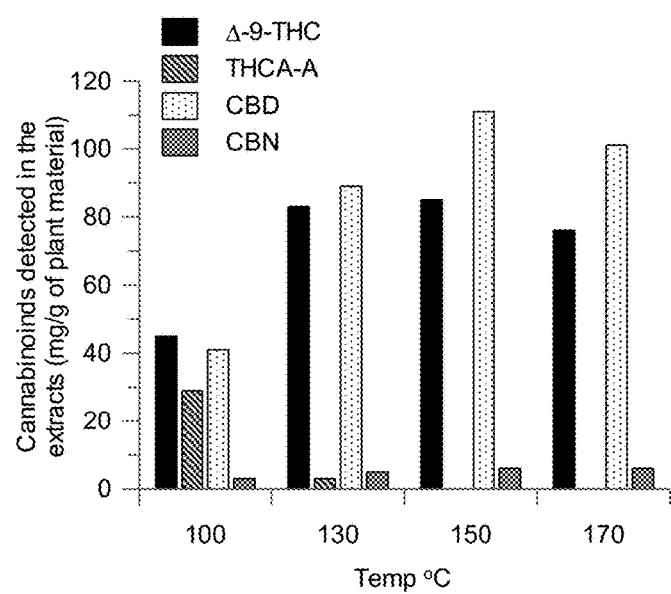
FIG. 13 shows various cannabinoid concentrations from *cannabis* after microwave heating only at various temperatures.
Figure 14:
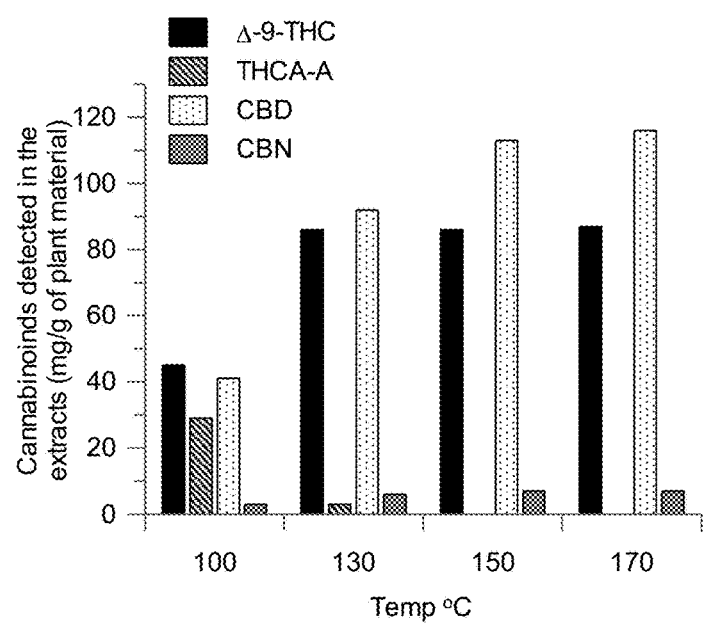
FIG. 14 shows various cannabinoid concentrations from *cannabis* after microwave heating and subsequent SFE extraction at various temperatures.

FIGS. 13 and 14 further show that high concentrations of THC, CBD, CBN and THCA in the extract are achieved when the extract is exposed to microwave radiation at about 170° C. for about 20 minutes. Further details regarding working variables are provided below.

Drying 102

At step 102, *cannabis* plant material can be dried to reduce water/moisture content. Herein, *cannabis* plant material encompasses any *cannabis* plant, including but not limited to *Cannabis sativa, Cannabis* indica and *Cannabis ruderalis*, and all subspecies thereof (for example, *Cannabis sativa* subspecies *indica* including the variants var. *indica* and var. *kafiristanica*), including wild or domesticated type *Cannabis* plants and also variants thereof, including *cannabis* chemovars (varieties characterized by virtue of chemical composition) which naturally contain different amounts of the individual cannabinoids and also plants which are the result of genetic crosses, self-crosses or hybrids thereof. The term "*cannabis* plant material" is to be interpreted accordingly as encompassing plant material derived from one or more *cannabis* plants. "*Cannabis* plant material" includes live or fresh *cannabis* and dried *cannabis*. In addition, any part of the *cannabis* plant may be used, including but not limited to trichomes, flower buds, flower bracts, leaves, stalk and any other plant part that may contain cannabinoids. Also, although the female plants may produce a higher concentration of cannabinoids than male plants, both female (including "feminized plants") and male plants can be used.

Optional drying step 102 can be used to remove excess moisture from the *cannabis* plant material prior to the *cannabis* plant material undergoing extraction and decarboxylation. Removing water content from the *cannabis* plant material can help to provide even heating at later stages in the extraction and/or decarboxylation process. Alternatively, fresh *cannabis* plant material (e.g. from the plant directly) can be used for the subsequent break down, extraction and decarboxylation steps. Herein, drying of the *cannabis* plant material at step 102 can occur by any means, for example in an oven at temperatures in the range of 60-75 C, or similar conditions, or using a vacuum oven or similar conditions over several hours, for example 4 hours, or 6 hours or 8 hours, depending on the amount of moisture. During the drying process, when heating is employed using heating elements in the ovens or infrared heating among other processes, some of the cannabinoid carboxyl acids forms could be converted into their decarboxylated cannabinoid forms.

Break Down 104

At break down step 104, *cannabis* plant material can be broken down to produce a *cannabis* plant material of a size and form suitable for extraction and decarboxylation by subjecting to microwave heating.

Trichomes (i.e. resin glands) of the *cannabis* plant material are nearly microscopic, mushroom-like protrusions from the surface of the buds, fan leaves, and the stalk. While relatively complex, trichomes are comprised primarily of a stalk and a head. The production of cannabinoids such as THC occurs predominantly in the head of the trichome. Cannabinoids are concentrated in the trichomes of the plant. The trichome is built to easily shed from the *cannabis* plant material surface.

The term "a size and form suitable for extraction and decarboxylation" refers to a reduction in the particle size of the *cannabis* plant material fragments.

Herein, breakdown of the *cannabis* plant material at step 104 can occur by any mechanical means including by crushing, smashing, grinding, pulverizing, macerating, disintegration or equivalent processes as are known to those skilled in the art that reduce the *cannabis* plant material into small pieces suitable in size and form for extraction and/or decarboxylation.

In one example embodiment, sonication can also be used to loosen the *cannabis* plant material in contact with an appropriate solvent such as ethanol, and/or by breaking down cellular membranes making it suitable for extraction and/or decarboxylation. In another example embodiment, maceration can be performed with a mortar and pestle to produce a *cannabis* plant material of a size and form suitable for extraction and/or decarboxylation.

In certain embodiments, the *cannabis* plant material is reduced in size such that its particle size is within a range of 1 mm to 10 mm.

Extraction 106

Upon completion of break down step 104, extraction step 106 may be performed. It should be noted that extraction step 106 may occur as a separate step to decarboxylation step 108 either before or after decarboxylation step 108, or as will be described below, extraction step 106 and decarboxylation step 108 may occur concurrently. For the avoidance of doubt it should be understood that any extraction, including but not limited to sonication in the presence of a solvent, reflux (Soxhlet) extraction and supercritical fluid extraction (SFE) may occur before or after decarboxylation step 108. In addition, it should also be understood that break down (104), extraction (106) and decarboxylation (108) may also occur in one step.

In one embodiment, extraction step 106 can comprise contacting cannabinoids from the broken down *cannabis* material that is the product of break down step 104 with a solvent.

In some embodiments, the solvent treatment in extraction step 106 removes non-cannabinoid impurities to leave a substantially pure preparation of cannabinoids. It has been shown that non-polar, liquid solvents may be useful for this function. Suitable non-polar solvents therefore include essentially any non-polar solvents which are substantially less polar than the cannabinoids, such that impurities which are more polar than the cannabinoids are removed by treatment with the solvent. Filtration and other methods as is known to those skilled in the art can also be used to remove impurities.

Useful non-polar solvents include, but are not limited to, C5-C12 straight chain or branched chain alkanes, or carbonate esters of C1-C12 alcohols. The more volatile C5-C12 alkanes may be particularly useful, as they are more easily removed from the extract. Further, solvents that have been approved for use in pharmaceutical compositions, such as ethanol (e.g. 95% ethanol) may be particularly useful.

Particularly useful solvents include pentane, hexane, heptane, iso-octane and ethanol, and/or mixtures thereof or the like as is known to those skilled in the art.

In one embodiment of extraction step 106, broken down *cannabis* plant material can be added to a solvent and concurrently sonicated.

Herein, sonication refers to the application of ultrasonic vibration (e.g. >20 kHz) to fragment cells, macromolecules and membranes of the dried or undried *cannabis* plant material. Ultrasonic vibration can be provided by any means known in the art.

In one exemplary embodiment, sonication of a mixture of *cannabis* plant material and solvent can occur for 5-25 minutes at 25° C., where the ratio of *cannabis* plant material and solvent is such that all *cannabis* plant material is submerged in the solvent completely in the reaction vessel.

Upon the completion of sonication of the mixture of *cannabis* plant material and solvent, the solvent is removed from the mixture. Removal of the solvent can occur by any means known in the art, including but not limited to filtration and/or evaporation. One embodiment for filtering after sonication is vacuum filtering over a glass sintered funnel to separate the resultant extract in the filtrate and the plant material. The latter can then be subjected to further extractions such as Soxhlet or other solvent extractions as is known to those skilled in the art, for example, SFE.

In yet another embodiment of extraction step 106, cannabinoids can be extracted from *cannabis* plant material that is broken down in step 104 by reflux (Soxhlet) extraction.

During reflux (Soxhlet) extraction, *cannabis* plant material that is broken down in step 104 is generally suspended above a heated solvent in a receptacle. The solvent is heated to reflux in a distillation flask such that solvent vapor travels up a distillation arm and floods into the receptacle housing raw *cannabis* material. A condenser suspended above the raw *cannabis* material ensures that any solvent vapor rising above the raw *cannabis* material cools and subsequently drips back down into the receptacle housing the raw *cannabis* material. The receptacle slowly fills with warm solvent such that cannabinoids begin to dissolve into the warm solvent. When the receptacle fills, it is emptied by a siphon such that the solvent is returned to the distillation flask. This cycle may be allowed to repeat many times, over hours or days.

Preferably, reflux (Soxhlet) extraction occurs at a solvent temperature higher than the boiling point of the corresponding solvent used for extraction and is conducted over a period of approximately 3 to 5 hours.

Once extraction is complete, removal of the solvent can occur by any means known in the art, including but not limited to filtering and/or evaporation as previously described.

In place of either sonication or reflux (Soxhlet) extraction as described above, another embodiment of extraction step 106 encompassed by the subject application is the extraction of cannabinoids from *cannabis* plant material by SFE.

SFE refers to a process of separating one or more components (extractant) from another (matrix) using supercritical fluids as the extracting solvent. Extraction is usually from a solid matrix (e.g. *cannabis* plant material), but can also be from liquids or resinous material (for example, hash oil).

Although numerous supercritical fluids can be used, carbon dioxide ($CO_2$) is the most commonly used supercritical fluid for SFE. In other exemplary embodiments, $CO_2$ can be modified by co-solvents such as ethanol or methanol as is known to those skilled in the art.

Extraction conditions for supercritical fluids are above the critical temperature (for example, 31° C. for $CO_2$) and critical pressure (for example, 74 bar for $CO_2$). Addition of modifiers such as but not limited to ethanol can require altering these extraction conditions.

An exemplary SFE system contains a pump for $CO_2$ (as well as any other solvents), a pressure cell to contain the *cannabis* material, a means of maintaining pressure in the system and a collecting vessel. The liquid is pumped to a heating zone, where it is heated to supercritical conditions. It then passes into the extraction vessel, where it rapidly diffuses into the solid matrix and dissolves the *cannabis* material to be extracted. The dissolved material (for example, cannabinoids) is swept from the extraction cell into a separator at lower pressure, and the extracted material settles out. The $CO_2$ can then be cooled, re-compressed and recycled, or discharged to atmosphere.

Herein, the temperature of the SFE extraction performed at extraction step 106 can, in some embodiments, be in the range of 35-55° C.

Further the pressure the SFE extraction performed at extraction step 106 can in some embodiments be in the range of 65-85 bar.

SFE in the present disclosure occurs at about 40° C. with a back pressure regulator pressure of 12 MPa and the extracted compounds are monitored using a photodiode array of 200-600 nm (monitoring at 254 nm). The acquisition time and method times of the system can each vary by a few minutes up to 60 minutes, ideally between 15 and 30 minutes, depending on the ratio of supercritical fluid and the co-solvent is altered for the extraction.

In specific embodiments, SFE can be carried out multiple times in succession. In such embodiments, the SFE is a fractional SFE.

As previously described for sonication with a solvent and reflux (Soxhlet) extraction, once SFE is complete, removal of the solvent can occur by any means known in the art, including but not limited to filtering and/or evaporation.

Microwave-Assisted Extraction and Decarboxylation 108

Decarboxylation of phytocannabinoid acids such as $\Delta^9$-THC-A is a function of the time and temperature of the reaction. For instance, the decarboxylation of concentrated $\Delta^9$-THC-A in solution into $\Delta^9$-THC and the degradation of $\Delta^9$-THC vary with temperature. Temperature controls are therefore important for controlling desired ratios of decarboxylation products. The use of conventional household microwaves in the processing of *cannabis* has been discussed in the literature, however, with mixed, inconsistent results and not necessarily specifically for extraction in a solvent and decarboxylation. Further, in order to obtain 100% decarboxylation, the temperature must be sustained over a period of time without burning of the *cannabis* material or boiling/evaporation of the solvent. If the temperature is higher than the boiling point of the solvent employed, the solvent will boil over and/or evaporate. In order to sustain the temperature over the required period of time to fully decarboxylate the cannabinoids but not burn the *cannabis* plant material or boil/evaporate the solvent with the *cannabis*, the microwave vessel (i.e. the sealed container) must be under pressure. Sealing the vessel or container ensures pressure in the vessel or container.

As shown in FIG. 3, microwave-assisted extraction can occur either immediately after mechanical breakdown step 104 or after a preliminary extraction step 106 as described above.

Microwave assisted extraction and decarboxylation 108 can comprise suspending *cannabis* plant material in a solvent and subjecting the mixture to microwaves in a closed container at a temperature, pressure and time sufficient to form decarboxylated cannabinoids.

Herein, the term "microwaves" refer to a form of electromagnetic radiation with wavelengths ranging from one meter to one millimeter; with frequencies between 300 MHz (100 cm) and 300 GHz (0.1 cm).

Further, solvent treatment in microwave assisted extraction and decarboxylation step 108 is again to remove non-cannabinoid impurities to leave a substantially pure preparation of cannabinoids. As such, non-polar, liquid solvents are useful for this function. In one embodiment, ethanol is used as the liquid solvent in microwave assisted extraction and decarboxylation step 108. In another embodiment, 95% ethanol is used as the liquid solvent in microwave assisted extraction and decarboxylation step 108.

As ethanol has a boiling point of 78° C. and the decarboxylation process of *cannabis* is temperature dependent (as described above), temperature control is important in microwave-assisted extraction step 108.

In one exemplary embodiment, suitable conditions to promote decarboxylation of CBDA and THCA to CBD and THC, respectively, are to suspend the *cannabis* plant material in a solvent (such as ethanol) and then subject this mixture to electromagnetic radiation (for example, microwaves) of a wavelength in the range of $10^6$-$10^9$ nm and a frequency of 300 MHz-300 GHz. In one embodiment, the conditions further include, for example, the following: temperature range of 40-250° C., temperature increase of 2-5° C./sec, pressure range of 0-20 bar (2 MPa, 290 psi), microwave power range of 0-400 W at 2.45 GHz or minor variations and adjustments to suit a particular solvent and/or reaction conditions to reach the required temperature and accomplish decarboxylation. If stirring is required, a variable magnetic stirrer (300-900 RPM) may be used.

In another exemplary embodiment, microwave assisted extraction and decarboxylation can be performed at a temperature in the range of 100-200° C. (including all possible integers and fractions of integers in this range, for example, 163.5° C.), 130-170° C., 150-170° C. or 130-150° C.

In another exemplary embodiment, microwave assisted extraction and decarboxylation can be performed at a pressure in the range of 2-22 bar (including all possible integers and fractions of integers in this range), for example, 10.7 bar or 17 bar or 18 bar or 19 bar or 20 bar or 21 bar.

The *cannabis* plant material can be suspended in a solvent and subjected to microwaves at frequency and wavelength of 2.45 GHz and $1.22 \times 10^8$ nm, respectively, and a temperature in the range of 130-190° C.

The raw *cannabis* material can be suspended in a solvent and subjected to microwaves at frequency and wavelength of 2.45 GHz and $1.22 \times 10^8$ nm, respectively, and a temperature in the range of 150-190° C. and the solvent is ethanol.

In another embodiment, *cannabis* plant material can be suspended in a solvent and the mixture stirred for a defined period of time (e.g. 0-30 sec or a reasonable length of time so as to suspend the material) before being subjected to microwaves. In one embodiment, the defined period is 30 seconds.

In another embodiment, *cannabis* material can be suspended in a solvent and the mixture can be stirred while being subjected to microwaves. In one embodiment, the defined period is 10 minutes and in another embodiment the defined period is 20 minutes. A table of working microwave variables is provided below for reference.

TABLE 1

| Temperature (° C.) | Total time (mins) | Pre-stirring (sec) | Stir rate (rpm) | Power supplied (W) | Holding Power (W) | Reaction Pressure (Bar) |
|---|---|---|---|---|---|---|
| 150 | 20 | 30 | 900 | 400 | 60 | 12 |
| 150 | 20 | 30 | 900 | 400 | 60 | 11 |
| 150 | 20 | 30 | 900 | 400 | 60 | 10 |
| 150 | 20 | 30 | 900 | 400 | 55 | 13 |
| 150 | 20 | 30 | 900 | 400 | 60 | 13 |
| 150 | 20 | 30 | 900 | 400 | 60 | 12 |
| 170 | 15 | 30 | 900 | 400 | 70 | 18 |
| 150 | 10 | 30 | 600 | 295 | 38 | 8.5 |
| 150 | 10 | 30 | 600 | 270 | 40 | 8.5 |
| 150 | 10 | 30 | 600 | 360 | 40 | 9 |
| 150 | 10 | 0 | 600 | 400 | 75 | 8 |
| 150 | 10 | 0 | 600 | 400 | 75 | 8.5 |
| 150 | 10 | 0 | 600 | 400 | 75 | 8.5 |
| 100 | 30 | 0 | 600 | 150 | 38 | 1 |
| 100 | 30 | 0 | 600 | 113 | 38 | 2 |
| 100 | 30 | 0 | 600 | 145 | 30 | 1 |
| 150 | 10 | 30 | 600 | 265 | 60 | 8 |
| 150 | 10 | 30 | 600 | 255 | 38 | 9 |
| 150 | 10 | 30 | 600 | 260 | 40 | 8.5 |
| 170 | 10 | 30 | 600 | 310 | 40 | 17 |
| 150 | 10 | 30 | 600 | 280 | 38 | 10 |
| 130 | 10 | 30 | 600 | 250 | 30 | 5 |
| 100 | 5 | 30 | 600 | 400 | 30 | 2 |
| 100 | 5 | 30 | 600 | 390 | 40 | 2 |

The parameters below can be set by the user, depending on the type of microwave equipment employed and the options available for user settings:

Power (OFF)=Constant power or the maximum power applied when heating the reaction mixture.

Initial Power (OFF)=Power applied initially when heating the reaction mixture.

Fixed Hold Time (ON)=If ON, the time countdown starts when the target temperature or target pressure is reached, i.e. the initial time taken to reach the set temperature or pressure is not included in the heating time.

Pressure (OFF)=Target pressure for reaction.

Cooling (OFF)=If OFF, cooling is not applied during the heating process. Absorption (NORMAL)=If NORMAL, power applied is initially between 200 and 400 W, depending on the target temperature.

Temperature=Target temperature. (Note: The temperature is monitored by an external infrared sensor that measures the surface temperature of the glass vial in real time.)

Total time=Total time for all steps.

Pre-stirring=Stirring time before heating process.

Stir-rate=Rotational speed of magnetic stir bar.

The parameters below were observed and extrapolated.

Power supplied=Power used to achieve the target temperature.

Holding power=Power used to maintain the target temperature.

Reaction pressure=Maximum pressure during the reaction.

In some embodiments, the decarboxylated cannabinoid product can be used directly or further processed, purified or recovered prior to use.

Recovery 110

Optionally, after being subjected to microwaves, a preparation of decarboxylated cannabinoids can be recovered from the resulting suspension at recovery step 110.

In one embodiment, extracted and decarboxylated cannabinoids are recovered by filtering the solvent from the extract of *cannabis* plant material to isolate the decarboxylated cannabinoids or decarboxylated cannabinoid comprising fraction.

In another embodiment, extracted and decarboxylated cannabinoids are recovered by filtering through an appropriate Celite® pad and/or activated carbon (e.g. charcoal) to obtain clarified solution for subsequent processing or use. In this embodiment, Celite® can be placed in a glass sintered funnel and then layered with activated carbon. Filtering agents can be washed with ethanol via vacuum filtration and extract can be dissolved in appropriate volume of suitable solvent such as ethanol and transferred to a funnel. Vacuum can then be applied and the filtering agent can be washed with the solvent until cannabinoids are completely eluted. The resulting filtrate can then be concentrated to dryness (e.g. at 25° C.). Someone with skill in the art can also conceive employing functionalized membranes, cellulose filters or the like to accomplish the above recovery task, instead of Celite® and activated carbon pad.

Alternatively, the resulting preparation of decarboxylated cannabinoids from step 108 can be collected and subsequently processed according to any of the extraction methods described in step 106, including but not limited to sonication, reflux (Soxhlet) extraction and/or SFE.

Uses and Products

The decarboxylated *cannabis* resins can be used (i) directly as a medicine, natural health product, or for recreational use, or (ii) as a raw material in the preparation of products, such as pharmaceutical, natural health products, or recreational use products for known uses of decarboxylated cannabinoid(s), such as known therapeutic or psychoactive uses.

In one embodiment, the decarboxylated resin of the disclosure can be used directly, for example as a medicine or as a natural health product.

In one embodiment, a pharmaceutical composition can be formed comprising the resulting decarboxylated cannabinoid resin produced by the methods disclosed, which can further comprise a suitable pharmaceutical acceptable carrier or excipient.

The pharmaceutical compositions of the present disclosure can additionally comprise one or more further active pharmaceutical ingredients in addition to decarboxylated cannabinoids.

Pharmaceutical compositions can be prepared in various dosage forms depending on the desired use and mode of administration, whether it is oral (e.g., tablet or liquid forms), a mist or other forms (aerosol, inhaler or intravenous suitable formulations), as desired, using techniques well known in the art.

Pharmaceutically acceptable carriers or excipients for various different dosage forms are well-known in the art and include carriers, diluents, fillers, binders, lubricants, disintegrants, glidants, colorants, pigments, taste masking agents, sweeteners, flavorants, plasticizers, and any acceptable auxiliary substances such as absorption enhancers, penetration enhancers, surfactants, co-surfactants, and specialized oils. The proper excipient(s) is (are) selected based in part on the dosage form, the intended mode of administration, the intended release rate, and manufacturing reliability. Examples of common types of excipients include various polymers, waxes, calcium phosphates, and sugars.

A person of skill in the art would reference known methods of pharmaceutical preparations, such as described in Remington: The Science and Practice of Pharmacy, 22$^{nd}$ Edition, Edited by Allen, Loyd V., Jr, 2012.

The present disclosure is described in the following Examples, which are set forth to aid in the understanding of the disclosure, and should not be construed to limit in any way the scope of the disclosure as defined in the claims which follow thereafter.

EXAMPLES

Experiment 1: Decarboxylated *Cannabis* Resin

Medicinal *cannabis* was subjected to extraction and chemical analysis by UPLC-MS.

Extraction Methodologies

FIG. 2A shows medical *cannabis* and decarboxylated *cannabis* resin. Four types of extraction methods were performed as shown in the corresponding flow charts in FIG. 29. (A) Ultrasonication (B) Sohxlet extraction (C) Supercritical Fluid Extraction (Omar, J. Olivares, M. et al. J. Sep. Sci. 2013, 36, 1397-1404, incorporated herein by reference). (D) Closed system microwave extraction (in ethanol, hexane or isopropanol or liquid $CO_2$), as described in experiments 5-9 below.

UPLC-MS Methodology. Cannabinoid standards, *cannabis* extracts and cannabinoids in the donor samples were analyzed using Waters® ACQUITY UPLC H-Class System equipped with Quaternary Solvent Manager and Sample Manager FTN. The detector used to monitor the samples was Waters® MS 3100 mass spectrometer. Benzophenone, caffeine or $\Delta^9$-THC-$d_3$ was used as an internal standard. Conditions are listed in Table 2.

TABLE 2

| UPLC-MS Chromatographic conditions |
|---|
| UPLC-MS Conditions |
| Column: BEH (2.1 × 50 mm, $C_{18}$, 1.7 μm) |
| Mass scan range (ESI +ve and −ve): 150-500 m/z |
| Flow rate: 0.6 mL/min |
| Solvent: $H_2O$ (0.1% formic acid; solvent A) |
| MeOH (0.1% formic acid; solvent B) |
| Gradient conditions: |
| 0-4.5 min: 30% A/70% B-100% B |
| 4.5-5.0 min: 100% B |
| 5.0-5.2 min: 100% B-30% A/70% B |
| 5.2-6.0 min: 30% A/70% B |

Extraction Results.

TABLE 3

Quantities of extracts and major cannabinoids obtained from extraction Methods A-D of Strain I.

| | | Extract | Cannabinoid in resin (%) | |
|---|---|---|---|---|
| Method | Plant used (g) | isolated (g) | Total $\Delta^9$-THC (THCA + THC) | Total CBD (CBDA + CBD) |
| A | 1.51 | 0.453 | 31.2 ± 0.5 | 66.1 ± 1.4 |
| B | 2.00 | 0.616 | 16.7 ± 0.2 | 33.3 ± 0.6 |
| C | 1.00 | 0.277 | 30.4 ± 0.9 | 59.3 ± 1.9 |
| D | 1.01 | 0.211 | 29.4 ± 7.6 | 33.8 ± 8.6 |

TABLE 4

Quantities of extracts and major cannabinoids obtained after Method D (closed system microwave extraction).

| Strain | Plant used (g) | Extract isolated (g) | Cannabinoid in resin (%) $\Delta^9$-THC | CBD |
|---|---|---|---|---|
| I | 1.01 ± 0.0003 | 0.211 ± 0.01 | 29.4 ± 7.6 | 33.8 ± 8.6 |
| II | 1.00 ± 0.0004 | 0.154 ± 0.004 | 1.9 ± 0.2 | 37.6 ± 4.1 |
| III | 1.00 ± 0.002 | 0.210 ± 0.009 | 49.8 ± 0.9 | 0 |

Chemical Analyses by UPLC-MS.

Mass spectra of Strain 1 before (FIG. 2b) and after (FIG. 2c) decarboxylation of medical *cannabis*, indicates 100% conversion of CBDA and THCA into CBD and THC, respectively.

Closed system microwave extraction provides simultaneously extraction and decarboxylation of the cannabinoids, as observed during chemical analysis by UPLC-MS.

Experiment 2: Further Comparison of Various Extraction Methods, Decarboxylation of Cannabinoids and Production of Standard Curves Method 1A: Ultrasonic Extraction (Sonication).
General Procedure:
1. Dried plant material was weighed and macerated using a mortar and pestle.
2. Solvent was added (25-130 mL) and mixture sonicated for 5 mins at 25° C.
3. Solvent was decanted and filtered over a glass sintered funnel using a vacuum filtration.
4. Steps 2 and 3 were repeated twice with the remaining fibre material.
5. Filtrate was concentrated to dryness (at 25° C.) then weighed (green resin).

Table 5 below shows the results of sonication of three common strains of *cannabis*.

TABLE 5

Results of sonication extraction with various solvents on three strains of cannabis.

| Strain | | Hexanes | Solvent Isopropanol/hexanes (1:1) | Ethanol |
|---|---|---|---|---|
| Cannabis strain 1 (THC: 7.18/CBD: 8.6) | Plant Used (g) | 0.256 | 1.0013 | 0.246 1.5084 |
| | Resin produced (g) | 0.0617 | 0.4748 | 0.1802 0.4531 |
| Cannabis strain 2 (THC: 0/CBD: 9) | Plant Used (g) | N/A | N/A | 2.0018 |
| | Resin produced (g) | N/A | N/A | 0.4795 |
| Cannabis strain 3 (THC: 18.6/CBD: 0) | Plant Used (g) | N/A | N/A | 2.9475 |
| | Resin produced (g) | N/A | N/A | 1.1611 |

Method 1B: Filtration Over Celite®/Activated Carbon.

Following Method 1A (described above), extracts were subjected to filtration over Celite® and activated carbon in order to eliminate the green colour of extracts. The results are shown in Table 6.

General Procedure:
1. Celite® was placed in a glass sintered funnel, then layered with activated carbon.
2. Extract was dissolved in 1 mL ethanol and transferred to funnel.
3. Vial that contained extract was washed twice with 1.5 mL ethanol and transferred to funnel.
4. Vacuum was then applied and filtering agent washed with ethanol until filtrate was no longer UV active (60-70 mL).
5. Filtrate was concentrated to dryness (at 25° C.), then weighed (orange resin).

TABLE 6

Results of extract filtration with Celite®/Activated Carbon for three strains of cannabis

| Strain | Extract used (g) | Extract isolated (g) |
|---|---|---|
| Cannabis strain 1 (THC: 7.18/CBD: 8.6) | 0.2265 | 0.2095 |
| Cannabis strain 2 (THC: 0/CBD: 9) | 0.2026 | 0.1717 |
| Cannabis strain 3 (THC: 18.6/CBD: 0) | 0.4984 | 0.4561 |

Method 2: Soxhlet Extraction
General Procedure:
1. Dried plant material was weighed and macerated using a mortar and pestle
2. Crushed material was then transferred to a cellulose extraction thimble (43×123 mm; 2 mm thickness)
3. Thimble was then inserted into a large extractor (size: 55/50)
4. Solvent (400 mL) and stir bar were added to a round bottom flask, which was then placed in the suitable DrySyn heating block and connected to the extractor
5. Extractor was then connected to a large condenser (size: 55/50) and refluxing was done at 120° C. for 3.5 hrs
6. Once refluxing was complete, the solvent was concentrated to dryness (at 25° C.) then weighed (green resin)

Table 7 below provides the results of Soxhlet extraction of *cannabis* according to the forgoing procedure.

TABLE 7

Results of Soxhlet extraction of cannabis.

| Strain | Amount of plant used (g) | Extract isolated (g) |
|---|---|---|
| Cannabis (THC: 7.18/CBD: 8.6) | 2.0021 | 0.6163 |

Method 3: Supercritical Fluid Extraction (SFE)
General Procedure:
1. Dried plant material was weighed and macerated using a mortar and pestle
2. Crushed plant material was transferred to a 10 mL extraction vessel and subjected to either of the following conditions below
3. All fractions were combined and concentrated to dryness (at 25° C.) then weighed (green resin)

Method 3A: SFE conditions
Solvent A=$CO_2$ Solvent B=ethanol
Temperature=40° C. BPR=12 MPa
PDA=200-600 nm (monitoring at 254 nm)
Acquisition time=30 mins Method time=30.2 mins
i. 5 mins static with 1:1 A/B
ii. 25 mins dynamic with 1:1 A/B (Flow rate=10 mL/min; make up pump=0.2 mL/min)
iii. Fractions were collected every 5 mins Method 3B: SFE conditions
Solvent B=ethanol
Solvent A=$CO_2$
Temperature=40° C. BPR=12 MPa
PDA=200-600 nm (monitoring at 254 nm)
i. 15 mins dynamic with 100% A (Flow rate=10 mL/min)
Fractions were collected every 7.5 mins
Acquisition time=15 mins Method time=15.2 mins
ii. 30 mins dynamic with 80:20 A/B (Flow rate=10 mL/min; make up pump=1 mL/min)
Fractions were collected every 5 mins
Acquisition time=30 mins Method time=30.2 mins Table 8 below shows the results of SFE according to the conditions outlined in Methods 3A and 3B for *cannabis*.

TABLE 8

Results of SFE extraction of cannabis according to two sets of conditions.

| Strain | Conditions | Amount of plant used (g) | Extract isolated (g) |
|---|---|---|---|
| Cannabis (THC: 7.18/CBD: 8.6) | Method 3A | 1.0047 | 0.2164 |
| | Method 3B | 1.0043 | 0.2561 |

Method 4: Microwave-Assisted Extractions with Ethanol (MAE) Followed by SFE.

Suitable conditions to promote decarboxylation of CBDA and THCA to CBD and THC, respectively, were determined with MAE.

The solvent used for this extraction was ethanol. However, since ethanol has a boiling point of 78° C., the highest temperature that could be achieved when heating only ethanol in a sealed vessel under microwave conditions had to be determined.

General Procedure:
1. Ethanol (11 mL) and a stir bar were placed in a 20 mL microwave vial which was then sealed.
2. General microwave conditions:
   a. Pre-stirring=30 secs
   b. Run time=15 mins
   c. Absorption=Normal The results are shown in Table 9 below.

TABLE 9

Determination of highest temperature that could be achieved when heating only ethanol in a sealed vessel under microwave conditions.

| Attempt # | Temperature (° C.) | Results |
|---|---|---|
| 1 | 200 | Maximum system pressure attained; Run aborted due to high pressure |
| 2 | 150 | Run completed |
| 3 | 190 | Maximum system pressure attained; Run aborted due to high pressure |
| 4 | 180 | Maximum system pressure attained; Run aborted due to high pressure |
| 5 | 170 | Run completed |

Once the maximum temperature that ethanol could be heated was determined, the following conditions were performed with *cannabis*:

General Procedure:
1. Dried plant material was weighed and macerated using a mortar and pestle
2. Crushed plant material was transferred to a 20 mL or 5 mL microwave vial along with a stir bar
3. Ethanol (11 mL or 3 mL) was added to the vial such that the plant material was completely submerged. The vial was then sealed and subjected to the microwave conditions below:
   a. Pre-stirring=30 secs
   b. Run time=10 mins
   c. Absorption=Normal
4. The suspension was filtered and the filtrate and plant fibre collected separately
5. Filtrate was concentrated and plant fibre subjected to the SFE conditions below:
   Solvent A=$CO_2$ Solvent B=ethanol
   Temperature=25° C. BPR=12 MPa
   PDA=200-600 nm (monitoring at 254 nm)
   Acquisition time=20 mins Method time=20.2 mins
6. Gradient from 100% A to 50%; 0.1 mins-15 mins (Flow rate=10 mL/min; make up pump=1 mUmin)
7. Fractions were collected every 7.5 mins The results are shown in Table 10 below.

TABLE 10

Extraction of cannabis by Microwave and SFE at various microwave temperatures

| Strain | Method | Temperature (° C.) | Amount of plant used (g) | Extract isolated after microwave (g) | Extract isolated after SFE (g) |
|---|---|---|---|---|---|
| Cannabis spp. (THC: 7.18/ CBD: 8.6) | A | 100 | 1.0012 | 0.3246 | N/A |
| | B | 130 | 0.2554 | 0.0592 | 0.0008 |
| | C | 150 | 0.2543 | 0.063 | 0.0005 |
| | D | 170 | 0.2554 | 0.0644 | 0.0025 |

Table 14 (provided below) shows the analyses and quantification of the cannabinoids.

Method 5. SFE/Soxhlet/Sonication Extraction Followed by Microwave of the Resin (for Decarboxylation).

General Procedure:
1. Resin isolated from Methods 1A (ethanolic extract), 2 and 3A were dissolved in 3-3.5 mL ethanol and transferred to a 5 mL microwave vial.
2. A stir bar was added and the vial sealed and subjected to microwave conditions below:
   a. Temperature=150° C.
   b. Pre-stirring=30 secs
   c. Run time=10 mins
   d. Absorption=Normal
3. The reaction mixture was then concentrated.

The results are shown in Table 11 below.

TABLE 11

Weights of resins after subjecting to microwave heating.

| Strain | Method | Amount of resin (g) | Resin isolated after microwave (g) |
|---|---|---|---|
| Cannabis spp. (THC: 7.18/ CBD: 8.6) | 1A (Sonication) | 0.2223 | 0.1692 |
| | 2 (Soxhlet) | 0.2651 | 0.2211 |
| | 3A (SFE; 50:50) | 0.2164 | 0.1884 |

Chromatography Analyses (HPLC/MS/PDA)

The chromatographic profiles of the *cannabis* extracts were determined by LC-PDA-MS equipped with a Waters® 2545 binary gradient module LC, Waters® PDA2998 photodiode array detector (190-800 nm) and a Waters® 3100 mass spectrometer (60-2000 Da).

LC was performed on an X-Bridge analytical C18 column (4.6 mm×150 mm, 5 um I.D.) with 1.5 mL/min flow rate. Mass spectra were recorded using ESI (+ve) mode. The injection samples were filtered using Millex-GV® Syringe Filters (0.22 pm, EMD Millopore).

Chromatographic conditions were as follows:
Mobile phase:
   A: Water/0.1% formic acid
   B: Methanol/0.1% formic acid
Gradient:
   0 to 25 min: 30% A/70% B→100% B
   25 to 28 min: 100% B
   28 to 30 min: 100% B→30% A/70% B
   30 to 35 min: 30% A/70% B
Injection volume: 10 μL
Flow rate: 1.5 mL/min
Total run time: 35 min
UPLC/MS.

The *cannabis* extracts and cannabinoid standards were analyzed using Waters® ACQUITY UPLC H-Class System equipped with Quaternary Solvent Manager, Sample Manager FTN, Acquity UPLC® BEH column (2.1×50 mm, C18, 1.7 μm). The sample injection plate and the column were maintained at 15° C. and 40° C., respectively. The detector used to monitor the samples was Waters® MS 3100 mass spectrometer.

Chromatographic conditions were as follows:
Mobile phase:
   A: Water/0.1% formic acid
   B: Methanol/0.1% formic acid
Gradient:
   0 to 4.5 min: 30% A/70% B→100% B
   4.5 to 5.0 min: 100% B
   5.0 to 5.2 min: 100% B→30% A/70% B
   5.2 to 6.0 min: 30% A/70% B
Injection volume: 2 μL
Flow rate: 0.6 mL/min
Total run time: 6 min Standard Curves for Cannabinoids:

Standard cannabinoids samples were purchased from Cerilliant-Certified Reference Standards in the form of 1.0 mg/mL solution in methanol.

1. $\Delta^8$-Tetrahydrocannabinol ($\Delta^8$-THC, Cat #. T-032, Lot FE10011501)
2. $\Delta^9$-Tetrahydrocannabinol ($\Delta^9$-THC, Cat #. T-005, Lot FE05271502)
3. $\Delta^9$-Tetrahydrocannabinolic acid A (THCA-A, Cat #. T-093, Lot ER02101506)
4. $\Delta^2$-Cannabidoil (CBD, Cat #. C-045, Lot FE012881502)
5. Cannabidiolic acid (CBDA, Cat #. C-144. Lot FE0181602)
6. Cannabinol (CBN, Cat #. C-046, Lot FE06081502)

The chemical structures of cannabinoids 1-6 are provided in FIG. 1.

Working stock solution of each standard sample was prepared using water/0.1% formic acid and methanol/0.1% formic acid. The final concentration of each stock sample was 50 pg/mL in 30% water/0.1% formic acid and 70% methanol/0.1% formic acid.

The stock samples (50 pg/mL) were diluted with mobile phase (30% water/0.1 formic acid and 70% methanol/0.1% formic acid) to obtain the following concentrations:
   0, 0.1, 0.5, 1.0, 2.5, 5.0, 7.5, and 10.0 pg/mL Not all the concentrations were included in the construction of the standard curve. Some of the cannabinoids (e.g. 0.1 or 10.0 pg/mL) were excluded due to very low signal of saturation level.

Each concentration was run in triplicate. 2 μL injections were made and the signal was recorded for up to 6 minutes. SIR +ve (311, 315, and 359 m/z) or SIR −ve (313 and 357) and mass scan (150-500 m/z) in positive mode were monitored and recorded. SIR chromatograms were integrated and the AUC was plotted vs. concentration (pg/mL).

TABLE 12

Cannabinoids standard curve-summary.

| Reference compound | Retention time (min) | Range (μg/mL) |
|---|---|---|
| $\Delta^2$-CBD | 1.70 | 0.1-10.0 |
| CBD-A | 1.90 | 0.01-1.0 |
| CBN | 2.33 | 0.1-7.5 |
| $\Delta^9$-THC | 2.58 | 0.1-7.5 |
| $\Delta^8$-THC | 2.70 | 0.1-10.0 |
| THCA-A | 3.42 | 0.01-1.0 |

Standard curves for each of cannabinoids 1-6 as described above are provided in FIGS. 4-9.

Figure 4:
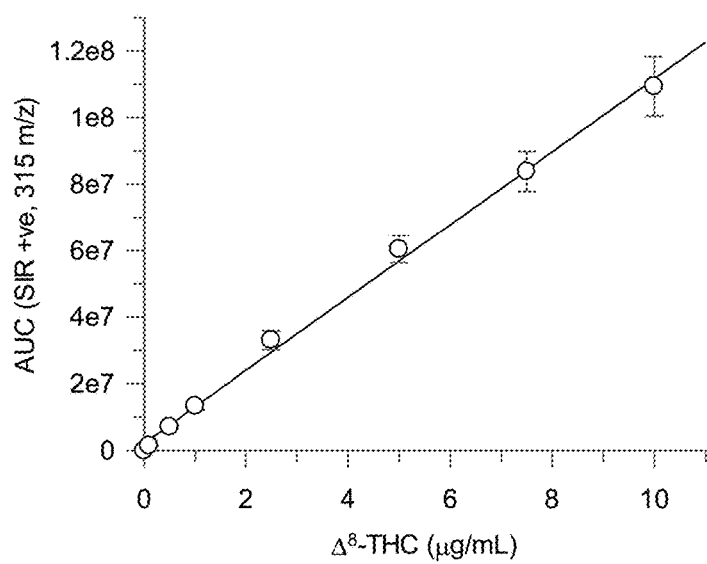
FIG. 4 shows a standard curve for $\Delta^8$-THC (selected ion recording (SIR) chromatograms were integrated and the AUC was plotted vs. concentration (ug/mL)

FIG. 4 shows a Standard Curve for $\Delta^8$-THC. Linear fit: y=10948149x+2153365, R=0.9984

Figure 5:
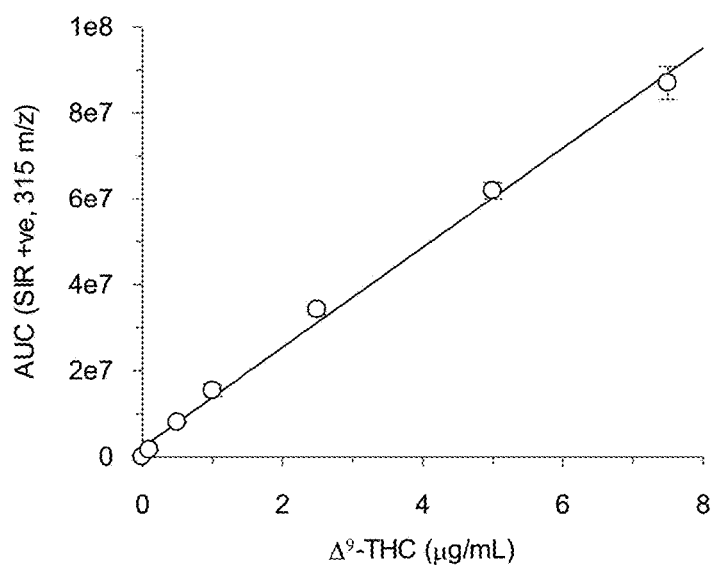
FIG. 5 shows a standard curve for $\Delta^9$-THC (selected ion recording (SIR) chromatograms were integrated and the AUC was plotted vs. concentration (ug/mL)

FIG. 5 shows a Standard Curve for $\Delta^9$-THC. Linear fit: y=11609869x+2187215, R=0.9980.

Figure 6:
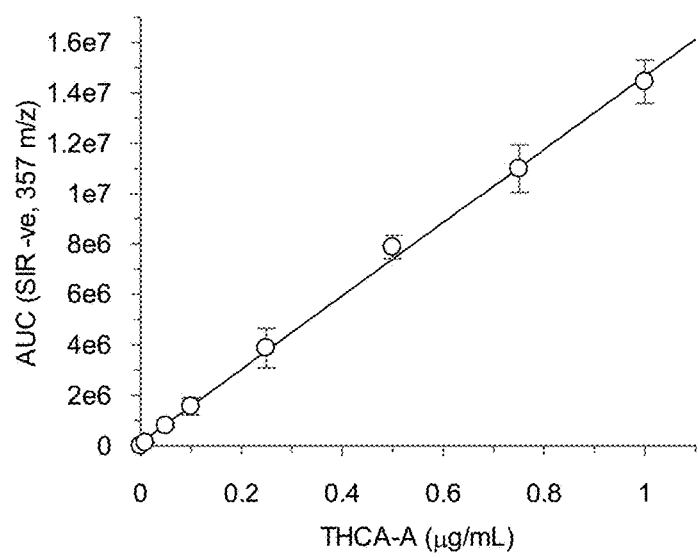
FIG. 6 shows a standard curve for THCA (selected ion recording (SIR) chromatograms were integrated and the AUC was plotted vs. concentration (ug/mL)

FIG. 6 shows a Standard Curve for THCA. Linear fit: y=14550967x+119886, R=0.9992

Figure 7:
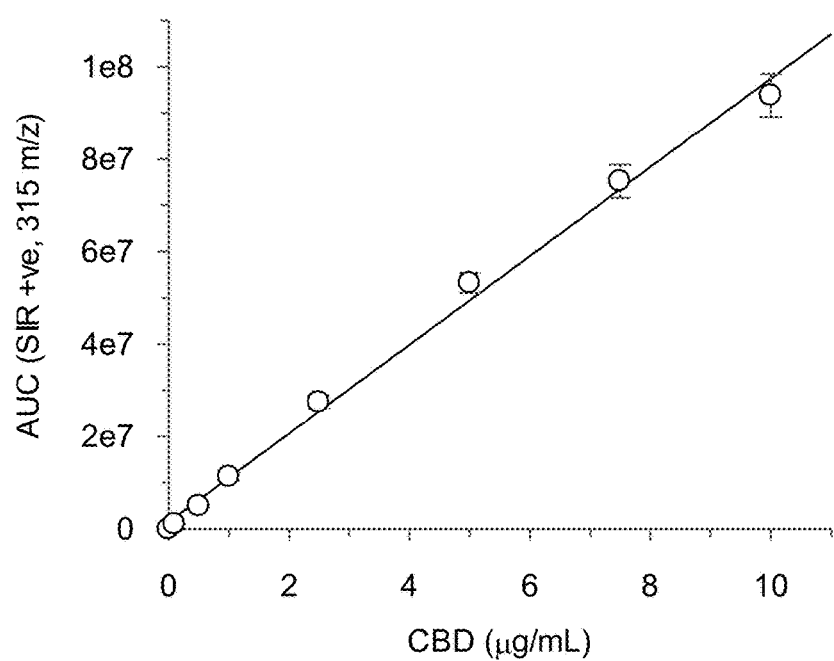
FIG. 7 shows a standard curve for CBD (selected ion recording (SIR) chromatograms were integrated and the AUC was plotted vs. concentration (ug/mL)

FIG. 7 shows a Standard Curve for CBD. Linear fit: y=9601901x+1448932, R=0.9978.

Figure 8:
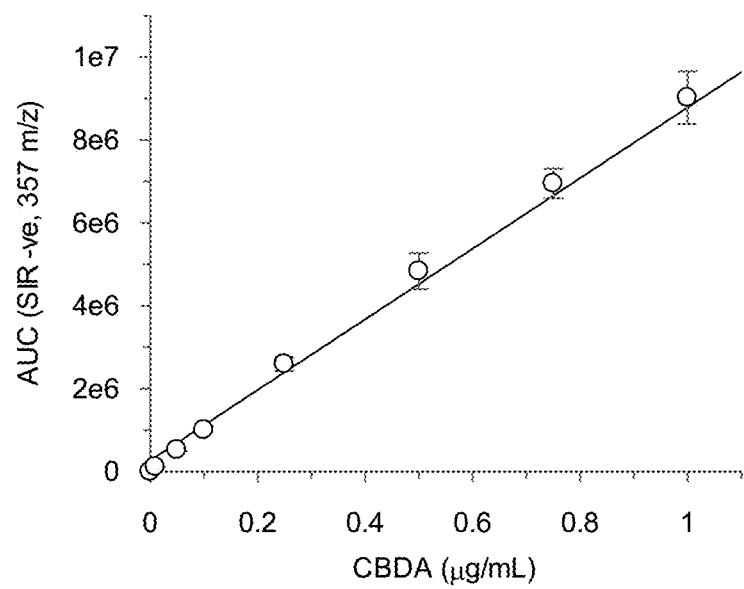
FIG. 8 shows a standard curve for CBDA (selected ion recording (SIR) chromatograms were integrated and the AUC was plotted vs. concentration (ug/mL)

FIG. 8 shows a Standard Curve for CBDA. Linear fit: y=9096880x+111409, R=0.9993.

Figure 9:
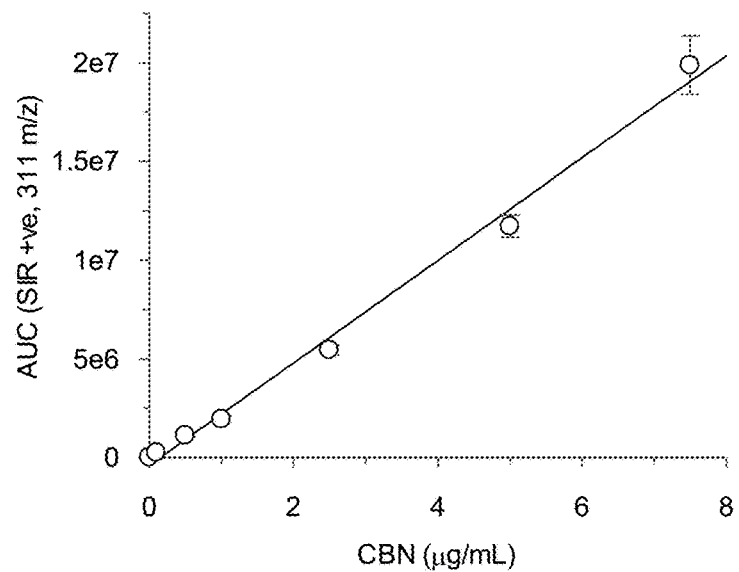
FIG. 9 shows a standard curve for CBN (selected ion recording (SIR) chromatograms were integrated and the AUC was plotted vs. concentration (ug/mL)

FIG. 9 shows a Standard Curve for CBN. Linear fit: y=2595328x−397594, R=0.9967.

Table 13 provides the concentration (pg/mL) of cannabinoids in extracts obtained using microwave extraction method at different temperatures. The solid material (plant fiber) leftover after the microwave reaction was exposed to SFE extraction (method 3A). The total volume of each microwave reaction was 3 mL.

TABLE 13

Concentration (μg/mL) of cannabinoids in extracts obtained using microwave extraction method at different temperatures

| Extraction conditions | $\Delta^8$-THC | $\Delta^9$-THC | THCA | CBD | CBN |
|---|---|---|---|---|---|
| Microwave, 100° C., 10 min; | 0 | 554 | 358 | 500 | 252 |
| No SFE done for this sample | N/A | N/A | N/A | N/A | N/A |
| Microwave, 130° C., 10 min | 0 | 7046 | 225 | 7565 | 443 |
| SFE | 0 | 243 | 0 | 302 | 32 |
| Microwave, 150° C., 10 min | 0 | 7201 | 0 | 9408 | 508 |
| SFE | 0 | 86 | 0 | 135 | 82 |
| Microwave, 170° C., 10 min | 0 | 6502 | 0 | 8566 | 495 |
| SFE | 0 | 936 | 0 | 1321 | 120 |

Figure 10:
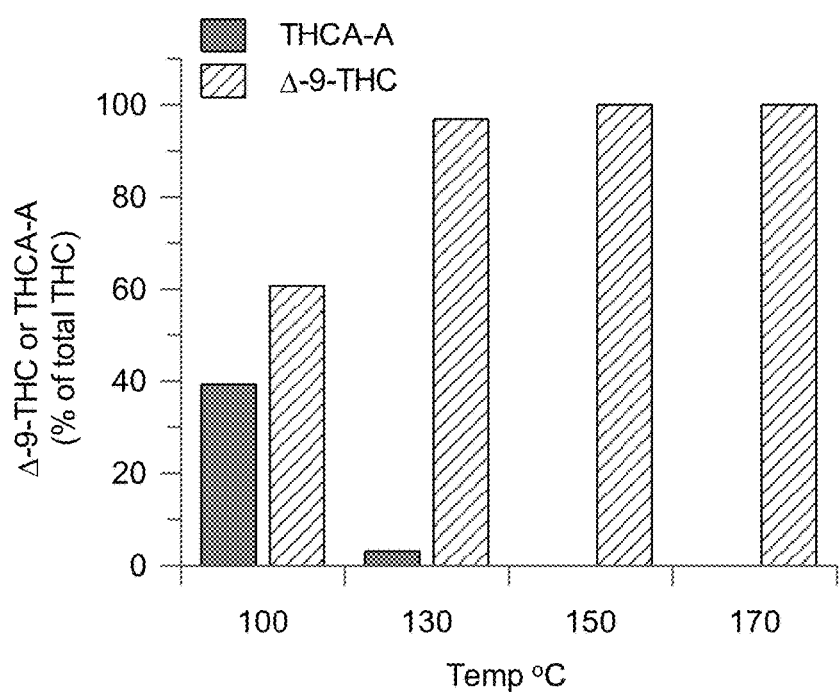
FIG. 10 shows a relative amount of $\Delta^9$-THC and THC-A present in *cannabis* plant material samples extracted using microwave radiation at various temperatures.

FIG. 10 shows the amount of $\Delta^9$-THC and THC-A present in samples extracted using microwave method at different temperatures. The amount of each form of THC is shown as a percentage of total amount of THC (neutral and acidic form).

Table 14 shows the amount of cannabinoids in the *cannabis* extracts, after subjecting to Method 5. See also Table 11. Note: CBN appears to be formed during the microwave based decarboxylation of THCA. CBDA was not quantified.

TABLE 14

Amount of cannabinoids in the cannabis extracts, after subjecting to Method 5

|  | $\Delta^8$-THC mg/g | $\Delta^9$-THC mg/g | $\Delta^9$-THCA-A mg/g | $\Delta^2$-CBD mg/g | CBN mg/g |
|---|---|---|---|---|---|
| Sonification (Method 1A) | 0 | 0 | 69.47 | 4.93 | 0 |
| Soxhlet alone (Method 2) | 0 | 44.32 | 40.71 | 25.4 | 0 |
| SFE alone (Method 3A) | 0 | 1.91 | 36.91 | 3.68 | 0 |
| Sonification + μw (Method 1A and 5) | 0 | 107.18 | 0 | 145.1 | 9.53 |
| Soxhlet + μw (Method 2 and 5) | 0 | 113.98 | 0 | 161.75 | 10.08 |
| SFE + μw (Method 3A and 5) | 0 | 96.48 | 0 | 122.66 | 8.96 |

μw = microwave
ND = not determined

A plot of the above data is shown in FIGS. 11 and 12, wherein FIG. 11 illustrates concentrations in the extracts using EtOH, Soxhlet and SFE, without subjecting *cannabis* to microwave conditions and FIG. 12 shows the concentrations of cannabinoids first extracting *cannabis* using EtOH or Soxhlet or SFE followed by microwave heating.

Table 15 shows the yield (mg/g of plant material) of cannabinoids in the extracts obtained using microwave extraction method at different temperatures. The solid material (plant fiber) left over after the microwave reaction was exposed to SFE extraction (method 3A). The total volume of each microwave reaction was 3 mL. CBDA was not quantified.

TABLE 15

Yield (mg/g of plant material) of cannabinoids in extracts obtained using microwave extraction method at different temperatures

| Conditions | $\Delta^8$-THC mg/g | $\Delta^9$-THC mg/g | THCA-A mg/g | CBD mg/g | CBN mg/g |
|---|---|---|---|---|---|
| Microwave 100° C., 10 min | 0 | 45 | 29 | 41 | 3 |
| No SFE | N/A | N/A | N/A | N/A | N/A |
| Microwave, 130° C., 10 min | 0 | 83 | 3 | 89 | 5 |
| Follow-up SFE | 0 | 3 | 0 | 4 | 0 |
| Microwave, 150° C., 10 min | 0 | 85 | 0 | 111 | 6 |
| Follow-up SFE | 0 | 1 | 0 | 2 | 1 |
| Microwave, 170° C., 10 min | 0 | 76 | 0 | 101 | 6 |
| Follow-up SFE | 0 | 11 | 0 | 16 | 1 |

FIG. 13 shows cannabinoids obtained from *cannabis* after microwave heating only.

FIG. 14 shows microwave followed by SFE extraction. The cannabinoids from microwave solvent and SFE extractions added together.

Figure 15:
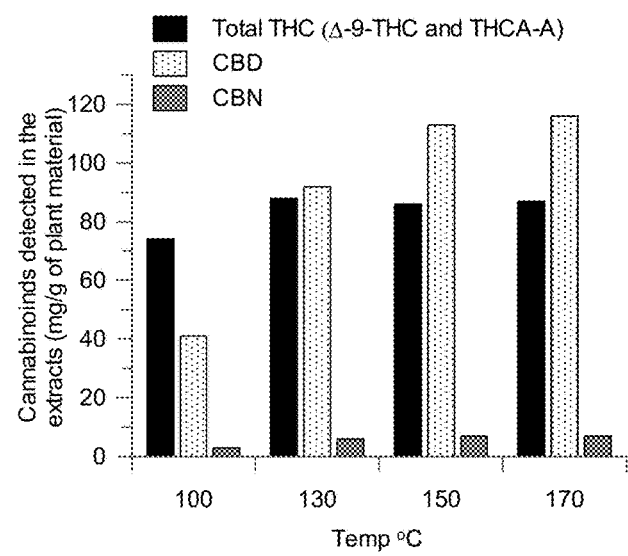
FIG. 15 shows various cannabinoid concentrations from *cannabis* after microwave heating and subsequent SFE extraction at various temperatures, where the acidic and neutral form of THC are added together to represent the total THC extracted by each method.

FIG. 15 shows various cannabinoid concentrations from *cannabis* after microwave heating followed by SFE extraction. In FIG. 15, the cannabinoids from both extractions have been added together. The acidic and neutral form of THC were added together to represent the total THC extracted by each method.

Figure 16:
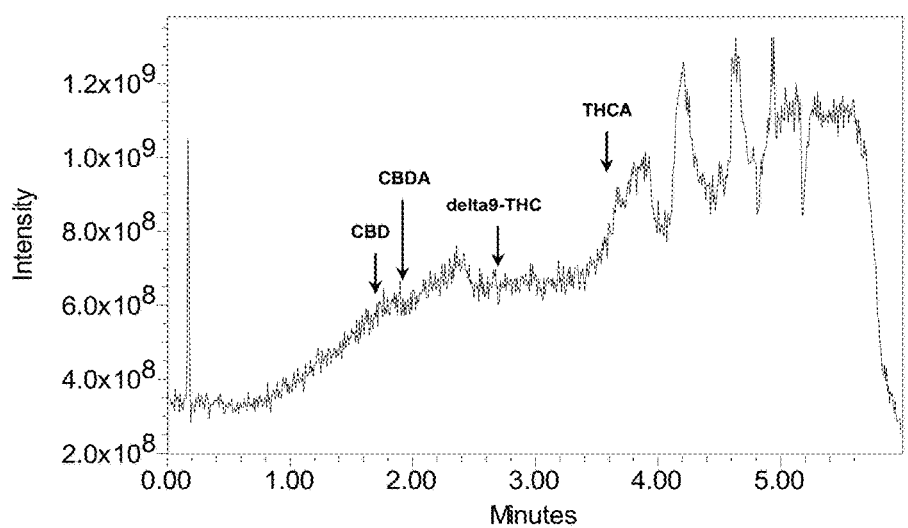
FIG. 16 shows a chromatogram of mass scan in a positive mode (150-500 m/z) of *cannabis* extract obtained from microwave extraction at 170° C., 15 min.
Figure 17:
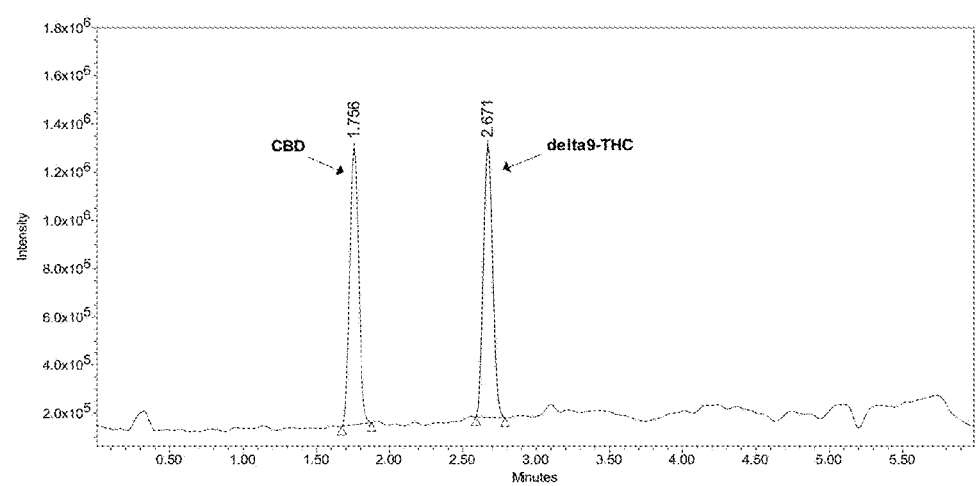
FIG. 17 shows single ion recording (SIR) (+ve) detection of m/z=315 for *cannabis* extract obtained from microwave extraction at 170° C., 15 min.
Figure 18:
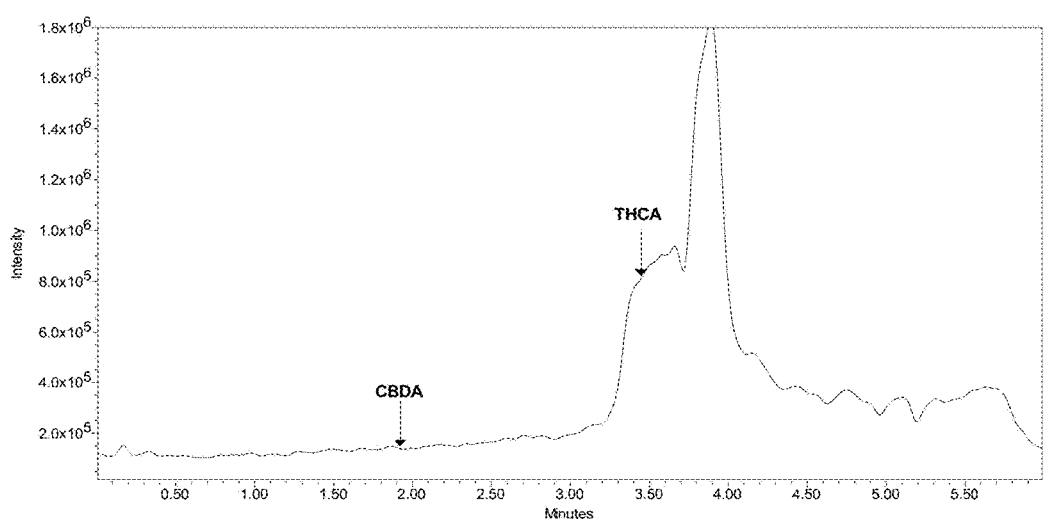
FIG. 18 shows SIR (+ve) detection of m/z=359 for *cannabis* extract obtained from microwave extraction at 170° C., 15 min.

FIG. 16 shows a chromatogram of mass scan (150-500 m/z) recorded in positive mode of ESI using Waters® MS3100 mass detector. The sample was obtained from microwave extraction at 170° C., 15 min. The arrows point to the retention times of CBD, CBDA, $\Delta^9$-THC, and THCA. Due to the low sample concentration the peaks are not visible in this chromatogram. Single ion recording (SIR +ve) obtained for this sample shows the individual peaks representing CBD and $\Delta^9$-THC (FIG. 17), CBDA and THCA (FIG. 18). If an analyte is absent or not detected in this mode, the expected retention time is shown FIG. 17 shows a Single Ion Recording (SIR +ve, m/z=315) to detect Cannabidiol (CBD) and $\Delta^9$-Tetrahydrocannabinol ($\Delta^9$-THC) in a sample obtained from microwave extraction at 170° C., 15 min (mass scan shown in FIG. 16).

FIG. 18 shows a Single Ion Recording (SIR +ve, m/z=359) to detect Cannabidiolic acid (CBDA) and Tetrahydrocannabinolic acid (THCA) in a sample obtained from microwave extraction at 170° C., 15 min (mass scan shown in FIG. 16). Positive mode (ESI+ve) is not a favorable one for the detection of the acidic forms of cannabinoids.

Figure 19:
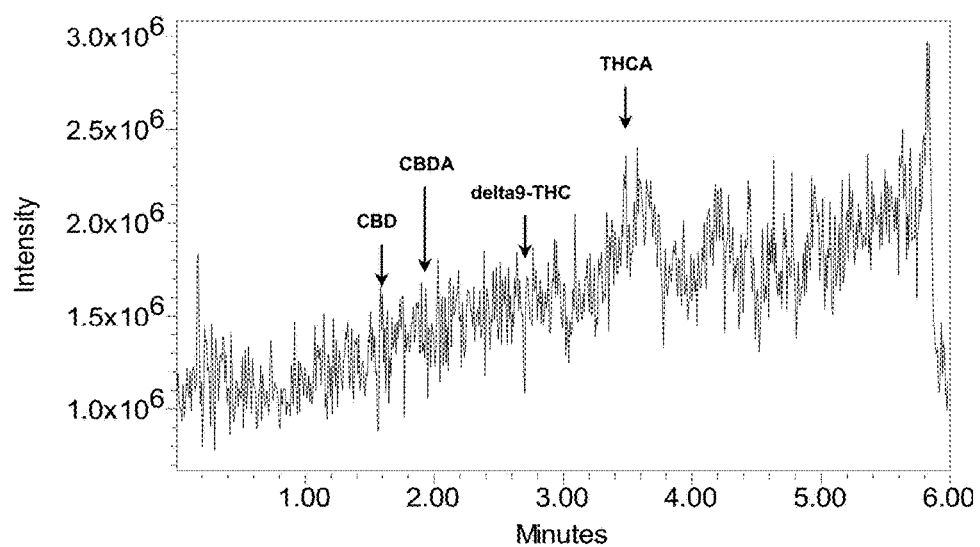
FIG. 19 shows a chromatogram of a mass scan in a negative mode (150-500 m/z) of *cannabis* extract obtained from microwave extraction at 170° C., 15 min.

FIG. 19 shows a chromatogram of mass scan (150-500 m/z) recorded in negative mode of ESI using Waters® MS3100 mass detector. The sample was obtained from microwave extraction at 170° C., 15 min. The arrows point to the retention times of CBD, CBDA, $\Delta^9$-THC, and THCA. Due to the low sample concentration the peaks are not visible in this chromatogram. Single ion recording (SIR −ve) obtained for this sample shows the individual peaks representing CBD and $\Delta^9$-THC (FIG. 20), CBDA and THCA (FIG. 21). If an analyte is absent or not detected in this mode, the expected retention time is shown.

Figure 20:
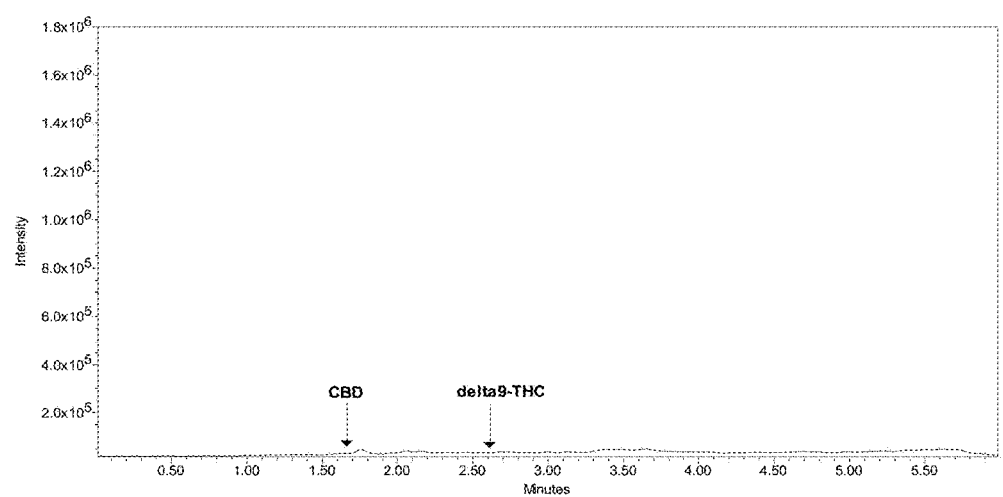
FIG. 20 shows SIR (−ve) detection of m/z=313 for *cannabis* extract obtained from microwave extraction at 170° C., 15 min.
Figure 21:
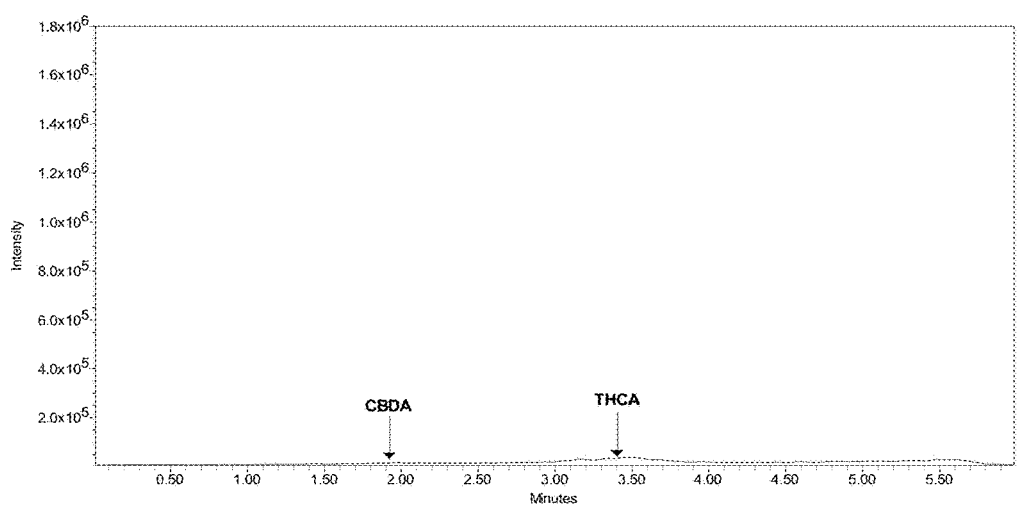
FIG. 21 shows SIR (−ve) detection of m/z=357 for *cannabis* extract obtained from microwave extraction at 170° C., 15 min.

FIG. 20 shows a Single Ion Recording (SIR −ve, m/z=313) to detect Cannabidiol (CBD) and $\Delta^9$-Tetrahydrocannabinol ($\Delta^9$-THC) in a sample obtained from microwave extraction at 170° C., 15 min (mass scan shown in FIG. 19). The neutral forms of cannabinoids are not easily detectable in the negative mode therefore no peaks observed as compared to the positive mode (see FIG. 17).

FIG. 21 shows a Single Ion Recording (SIR −ve, m/z=357) to detect Cannabidiolic acid (CBDA) and Tetrahydrocannabinolic acid (THCA) in a sample obtained from microwave extraction at 170° C., 15 min (mass scan shown in FIG. 19). ESI −ve mode is useful for the detection of the acidic forms of cannabinoids.

Figure 22:
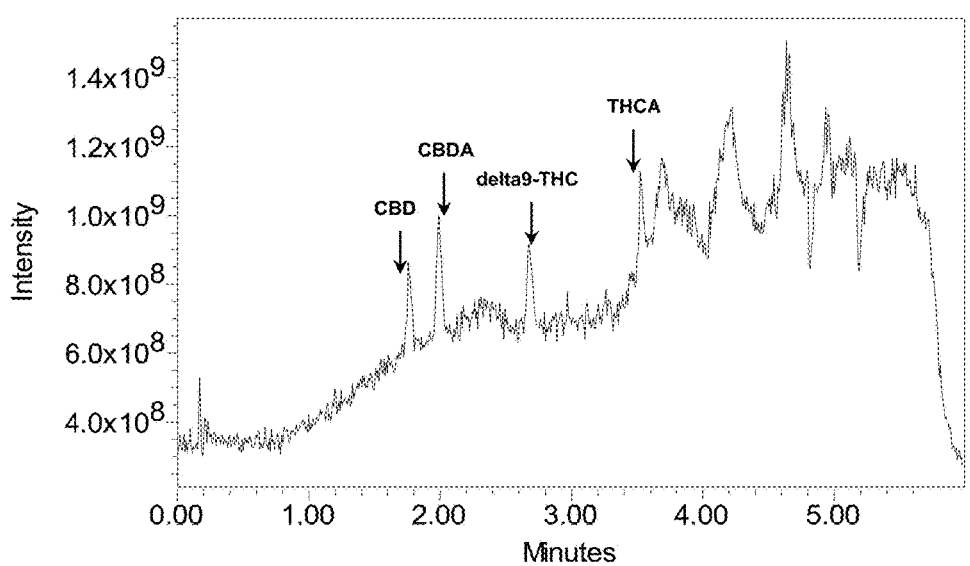
FIG. 22 shows a chromatogram of mass scan in a positive mode (150-500 m/z) of *cannabis* extract obtained from microwave extraction at 130° C., 10 min.

FIG. 22 shows a chromatogram of mass scan (150-500 m/z) recorded in positive mode of ESI using Waters® MS3100 mass detector. The sample was obtained from microwave extraction at 130° C., 10 min. Retention times of CBD, CBDA, $\Delta^9$-THC, and THCA are shown. Single ion recording (SIR +ve) obtained for this sample shows the individual peaks representing CBD and $\Delta^9$-THC (FIG. 23) and CBDA and THCA (FIG. 24). If an analyte is absent or not detected in this mode, the expected retention time is shown.

Figure 23:
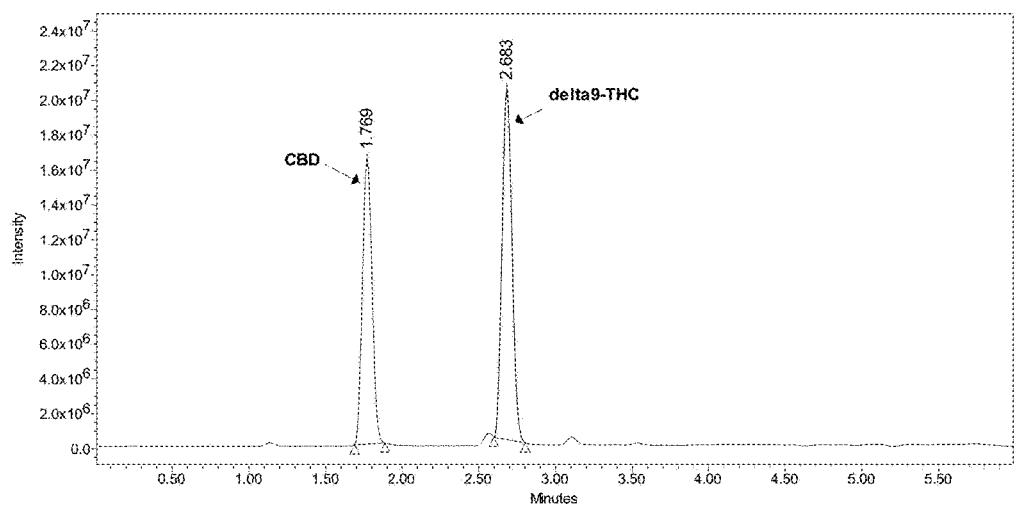
FIG. 23 shows SIR (+ve) detection of m/z=315 for *cannabis* extract obtained from microwave extraction at 130° C., 10 min.
Figure 24:
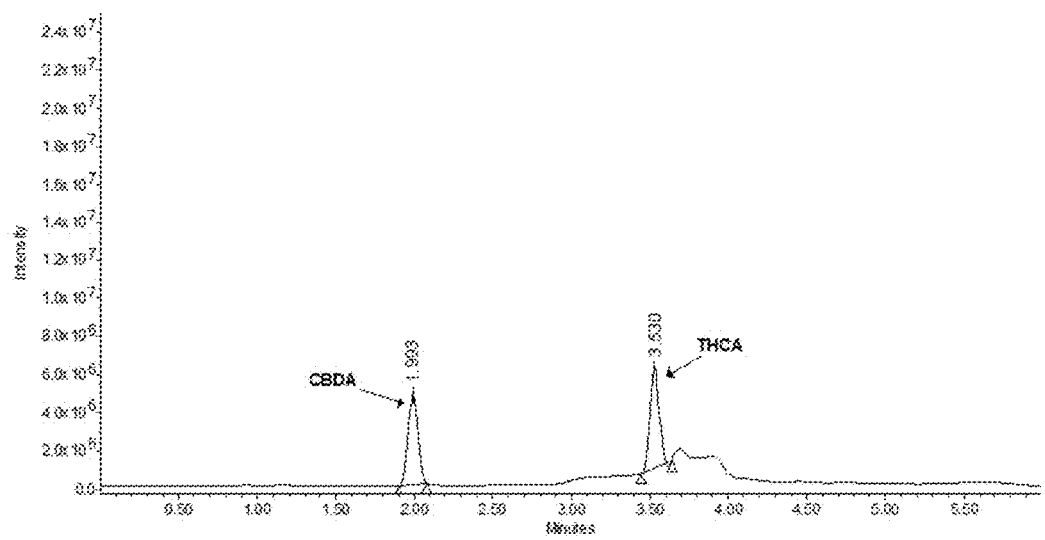
FIG. 24 shows SIR (+ve) detection of m/z=359 for *cannabis* extract obtained from microwave extraction at 130° C., 10 min.

FIG. 23 shows a Single Ion Recording (SIR +ve, m/z=315) to detect Cannabidiol (CBD) and $\Delta^9$-Tetrahydrocannabinol ($\Delta^9$-THC) in a sample obtained from microwave extraction at 130° C., 10 min (mass scan shown in FIG. 22).

FIG. 24 shows a single Ion Recording (SIR +ve, m/z=359) to detect Cannabidiolic acid (CBDA) and Tetrahydrocannabinolic acid (THCA) in a sample obtained from microwave extraction at 130° C., 10 min (mass scan shown in FIG. 22). Due to relatively high concentration of the analyzed sample the acidic forms of the CBD and THC are detected by the negative mode.

Figure 25:
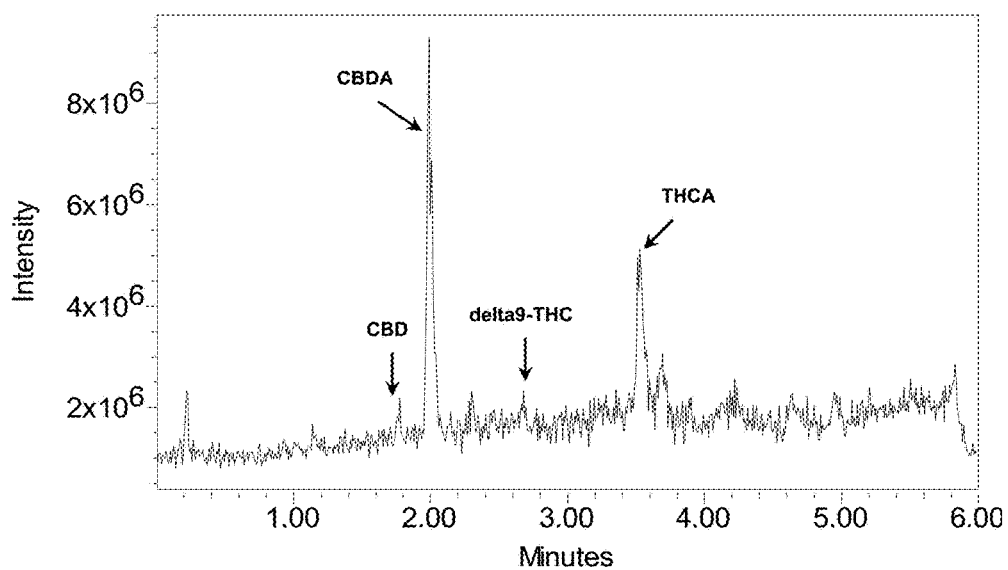
FIG. 25 shows a chromatogram of mass scan in a negative mode (150-500 m/z) of *cannabis* extract obtained from microwave extraction at 130° C., 10 min.
Figure 27:
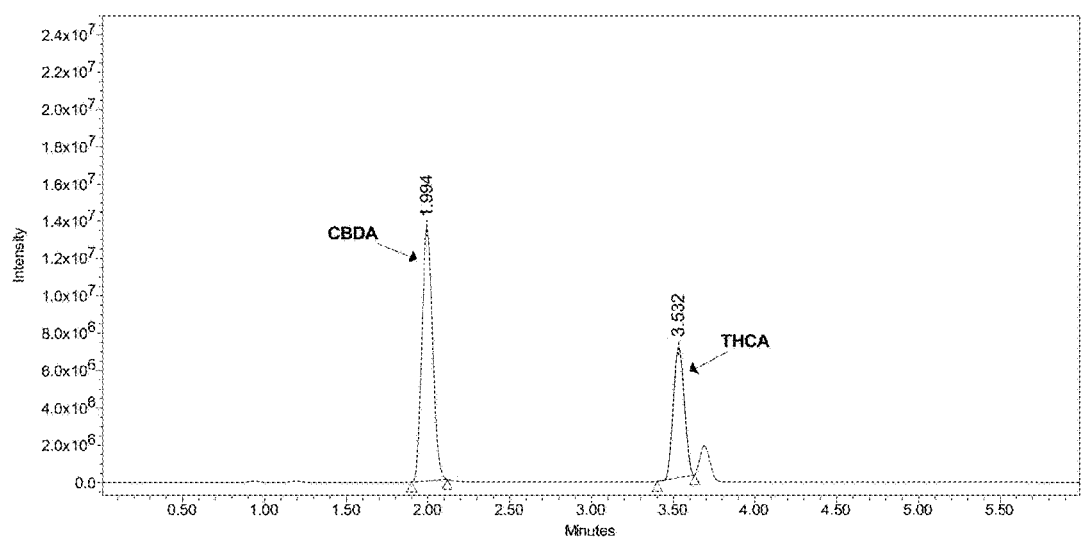
FIG. 27 shows SIR (−ve) detection of m/z=357 for *cannabis* extract obtained from microwave extraction at 130° C., 10 min FIG. 28A Overview of select signals as seen in the mass spectra before decarboxylation of *cannabis* extract FIG. 28B Overview of select signals as seen in the mass spectra after decarboxylation of *cannabis* extract FIG. 29A-D Shows flow charts of various extraction methods.

FIG. 25 shows a chromatogram of mass scan (150-500 m/z) recorded in negative mode of ESI using Waters® MS3100 mass detector. The sample was obtained from microwave extraction at 130° C., 10 min. Retention times of CBD, CBDA, $\Delta^9$-THC, and THCA are shown. Single ion recording (SIR −ve) obtained for this sample shows the individual peaks representing CBD and $\Delta^9$-THC (FIG. 26)

and CBDA and THCA (FIG. 27). If an analyte is absent or not detected in this mode, the expected retention time is shown.

Figure 26:
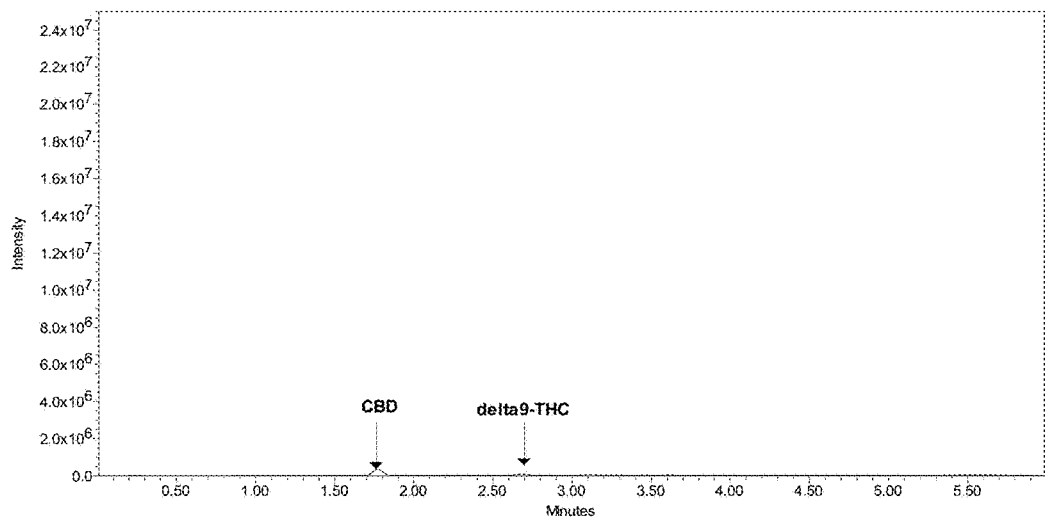
FIG. 26 shows SIR (−ve) detection of m/z=313 for *cannabis* extract obtained from microwave extraction at 130° C., 10 min.

FIG. 26 shows a Single Ion Recording (SIR −ve, m/z=313) to detect Cannabidiol (CBD) and $\Delta^9$-Tetrahydrocannabinol ($\Delta^9$-THC) in a sample obtained from microwave extraction at 130° C., 10 min (mass scan shown in FIG. 25). Neutral cannabinoids (CBD and $\Delta^9$-THC are not visible in the negative mode detection as compared to the positive mode (FIG. 23).

FIG. 27 shows a Single Ion Recording (SIR −ve, m/z=357) to detect Cannabidiolic acid (CBDA) and Tetrahydrocannabinolic acid (THCA) in a sample obtained from microwave extraction at 130° C., 10 min (mass scan shown in FIG. 25). Some CBDA and THCA still present showing partial decarboxylation.

Summary of results for experiment 2

FIGS. 4-9 provide standard chromatography curves for $\Delta^8$-THC, $\Delta^9$-THC, THC-A, CBD, CBDA and CBN, respectively. These standard curves were generated for concentrations between 0 and 10 pg/mL and subsequently used for determining the concentration of each compound in various products formed using the embodiments described herein.

Table 5 shows the use of various solvents during ultrasonic extraction. There were also minimal amounts of cannabis plant material lost during the recovery filtration process (see Table 6). This also appears to be similar recovery across different extraction methods—solvent, Soxhlet, SFE extraction (See Tables 7 and 8).

When conducting cannabinoid extraction/decarboxylation in ethanol using a microwave, due to the boiling point of ethanol, it was shown that extraction/decarboxylation of cannabinoids using a microwave is best conducted at temperatures below 180° C., for example at 160° C.±10° C. (e.g. +/−the acceptable standard of error). It was also shown under the conditions used that conversion of THCA to THC (the desired decarboxylated product) was better at 130° C. than at 100° C., and that if conducted using microwave alone versus microwave and SFE, temperatures above 130° C., for example from 150° C. to 170° C. showed more efficient conversion. (See Tables 13 and 15 as well as FIG. 10). However, there appears to be significant loss of material if followed by SFE (see Tables 9 and 10, and 15). As such, the least number of steps and processes to obtain the desired results is the one-step extraction/decarboxylation method.

FIGS. 11 and 12 and Table 14 show that extraction resulted in minimal or no decarboxylated THC product, while the addition of the microwave step resulted in a significant increase in decarboxylated THC.

FIG. 13 shows concentrations of $\Delta^9$-THC, THC-A, CBD and CBN from cannabis after microwave radiation only at temperatures ranging between 100° C. and 170° C. FIG. 13 shows that microwave radiation at temperatures between 130° C. and 170° C. were optimal when ethanol was used as the solvent.

FIG. 14 shows concentrations of $\Delta^9$-THC, THC-A, CBD and CBN from the cannabis plant material after microwave radiation and subsequent SFE extraction at temperatures ranging between 100° C. and 170° C. Use of SFE extraction does not appear to significantly increase yield of decarboxylated cannabinoids.

FIG. 15 shows concentrations of total THC, CBD and CBN from the cannabis after microwave radiation and subsequent SFE extraction at a temperatures ranging between 100° C. and 170° C., where the acidic and neutral form of THC are added together to represent the total THC extracted by each method. Again, use of SFE extraction does not appear to significantly increase yield of decarboxylated cannabinoids.

From the above results, it appears that the significant decarboxylated product THC results from microwave extraction and that the addition of a second extraction step, such as SFE, does not appear to change the cannabinoid profile. It further shows that CBD as well as THC components are present in extract after microwave extraction alone or with microwave and SFE extractions combined.

In summary, the present disclosure shows that extraction and decarboxylation of cannabis plant material can be done concurrently using a microwave, set at a temperature below the boiling point of the extraction solvent, such as ethanol, without the need for a separate extraction step. This optimizes decarboxylated cannabinoid formation and recovery and can produce a more consistent and reproducible product with consistent and reproducible efficacy and therapeutic results.

An extraction step can also be included before use of a microwave. Although an extraction step after the microwave step is possible, it is not necessary.

Experiment 3: Supercritical Fluid Extraction (SFE)

General Procedure:
1. Dried plant material was weighed and macerated using a mortar and pestle
2. Crushed plant material was transferred to a 10 mL extraction vessel and subjected to either of the following conditions below
3. Fractions from each run were collected every 5 mins and combined and concentrated to dryness (at 25° C.) then weighed (green resin)
4. Extraction was done three times with same plant fibre
   A) SFE conditions
   Solvent A=$CO_2$ Solvent B=ethanol
   Temperature=25° C. BPR=12 MPa PDA=200-600 nm (monitoring at 254 nm)
   Flow rate=10 mL/min; make up pump=1 mL/min
   Acquisition time=30 mins Method time=30.2 mins
   i. 0.1 min-25 mins; gradient of 0-50% B in A
   26 mins; 100% A
   30 mins; 100% A Table 16 below shows the corresponding results.

TABLE 16

| Weights of extract after SFE. | | |
|---|---|---|
| Strain | Run | Extract isolated (g) |
| Variety 1 = 1.0023 g | 1 | 0.2634 |
| (THC: 7.18/CBD: 8.6) | 2 | 0.0038 |
| | 3 | 0.010 |

Experiment 4: Microwave-Assisted Decarboxylation of Extract with Ethanol (MAE)

General Procedure:
1. Extract isolated from the SFE method described above was dissolved in 5-10 mL ethanol and an appropriate volume transferred to 5 mL microwave vials
2. Added additional volume of ethanol and a stir bar to the 5 mL microwave vials
3. The vials were sealed and subjected to one of two microwave conditions below:

(a) Temperature=150° C.; run time=10 mins; stir rate=600 rpm; absorption=Normal
(b) Temperature=100° C.; run time=30 mins; stir rate=600 rpm; absorption=Normal
4. The solution was then concentrated at 35° C. after transferring to 20 mL vials The results are shown in Table 17 below.

TABLE 17

Weights of the resins after subjecting to microwave heating.

| Strain | Method | Amount of resin used (g) | Extract isolated after microwave (g) |
|---|---|---|---|
| Variety 1 (THC: 7.18/CBD: 8.6) | (a) | 0.0832 | 0.0212 |
| | (b) | 0.0832 | 0.0612 |
| | (a) | 0.2095 | 0.1589 |
| Variety 2 (THC: 0/CBD: 9) | (a) | 0.1693 | 0.1114 |
| Variety 3 (THC: 18.6/CBD: 0) | (a) | 0.2722 | 0.1759 |

Experiment 5: Additional Microwave-Assisted Extractions with Ethanol (MAE), Optimization of Conditions for Decarboxylation General Procedure:
1. Dried plant material was weighed and macerated using a laboratory blender at 22,000 rpm for 60 secs
2. Crushed plant material was re-weighed and transferred to a 20 mL microwave vial along with a stir bar
3. Ethanol (10 mL) was added to the vial which was then sealed and subjected to the microwave conditions below:
   (a) Temperature=170° C.; run time=15 mins; pre-stirring=30 sec; stir rate=900 rpm; absorption=Normal
   (b) Temperature=150° C.; run time=20 mins; pre-stirring=30 sec; stir rate=900 rpm; absorption=Normal
4. The suspension was filtered and the filtrate and plant fibre collected separately
5. Filtrate was then concentrated at 35° C., then transferred to a 20 mL vial using ethanol and again concentrated at 35° C., then stored in the refrigerator The results are shown in Table 18 below.

TABLE 18

| Strain | Method | Amount of plant before maceration (g) | Amount of plant after maceration (g) | Extract isolated after microwave (g) |
|---|---|---|---|---|
| Variety 1 (THC: 7.18/CBD: 8.6) | (a) | 1.0062 | 0.8256 | 0.2265 |
| Variety 2 (THC: 0/CBD: 9) | (a) | 1.0042 | 0.8382 | —$^a$ |
| | (b) | 1.0050 | 0.8293 | 0.2155 |
| Variety 3 (THC: 18.6/CBD: 0) | (b) | 1.0063 | 0.7883 | 0.1166 |

$^a$Desired temperature could not be achieved due to pressure build-up; cap of vial popped off causing solvent and plant fibre to escape from vial.

Since condition (b) in step 3 above proved successful at that scale, subsequent decarboxylations were performed using that microwave condition and were done in triplicate. However, the following modifications were made:
Step 1: Blend at 18,000 rpm for 4 secs
Step 4: Filtration done over celite/activated carbon (as previously described in an earlier report)
Step 5: Filtrate was then concentrated at 35° C., weighed, transferred to a 20 mL vial using ethanol, then stored in the refrigerator The results are shown in Table 19 below.

TABLE 19

| Strain | Runs | Amount of plant before maceration (g) | Amount of plant after maceration (g) | Extract isolated (g) | Average Extract isolated (g) ± SD |
|---|---|---|---|---|---|
| Variety 1 (THC: 7.18/CBD: 8.6) | 1 | 1.0079 | 0.9260 | 0.2044 | 0.2105 ± 0.007 |
| | 2 | 1.0084 | 0.9594 | 0.2184 | |
| | 3 | 1.0080 | 0.9254 | 0.2088 | |
| Variety 2 (THC: 0/CBD: 9) | 1 | 1.0032 | 0.8287 | 0.1624 | 0.1654 ± 0.006 |
| | 2 | 1.0038 | 0.8467 | 0.1721 | |
| | 3 | 1.0040 | 0.8585 | 0.1617 | |
| Variety 3 (THC: 18.6/CBD: 0) | 1 | 1.0017 | 0.9169 | 0.2225 | 0.2212 ± 0.014 |
| | 2 | 1.0054 | 0.8952 | 0.2068 | |
| | 3 | 1.0033 | 0.9021 | 0.2343 | |

This experiments shows the consistency of the extraction method.

Experiment 6: *Cannabis* Extractions (1 Gram Scale)

General Procedure (~1.0 q Batch; Before Maceration):
1. Dried plant material was weighed and macerated using a laboratory blender at 18,000 rpm for 4 secs
2. Crushed plant material was re-weighed (~0.875 g) and transferred to a 20 mL microwave vial along with a stir bar
3. Ethanol (10 mL) was added to the vial which was then sealed and subjected to the microwave conditions below:
Temperature=150° C.; run time=20 mins; pre-stirring=30 sec; stir rate=900 rpm; absorption=Normal
4. The suspension was filtered over celite/activated carbon and the filtrate and plant fibre collected separately
5. Filtrate was then concentrated at 35° C., then transferred to a 20 mL vial using ethanol and again concentrated at 35° C., then stored in the refrigerator
6. Decarboxylations were performed in triplicate Winterization Procedure:
1. Resin was dissolved in ethanol (10 mUg) and heated at 40° C. for 5 mins in a water bath
2. Vial containing extract solution was cooled to −75° C. using a dry ice/acetone bath for 3-4 hrs
3. Solution was filtered with a pre-weighed syringe filter in 20 mL vials Filter specifications: Millex®-GV (sterile), Low Protein Binding Durapore® (PVDF) Membrane; 0.22 pm pore size; 33 mm diameter
4. Filter was washed with ethanol that had been cooled for 5 mins at −75° C. using a dry ice/acetone bath
5. Filtrate was concentrated at 35° C. and extract was weighed
6. Syringe filter was weighed after 2-3 days drying in the fumehood

TABLE 20

The quantities of cannabis plants used and the amounts of extract obtained before and after winterization.

| Strain | Runs | Plant before maceration (g) | Plant after maceration (g) | Extract isolated before winterization (g) | Extract isolated after winterization (g) |
|---|---|---|---|---|---|
| Variety 1 (THC: 7.18/CBD: 8.6) | 1<br>2<br>3 | 1.008 ± 0.0003 | 0.9369 ± 0.019 | 0.2105 ± 0.007 | 0.1962 ± 0.007 |
| Variety 2 (THC: 0/CBD: 9) | 1<br>2<br>3 | 1.004 ± 0.0004 | 0.8446 ± 0.015 | 0.1654 ± 0.006 | 0.1541 ± 0.004 |
| Variety 3 (THC: 18.6/CBD: 0) | 1<br>2 | 1.003 ± 0.0019 | 0.9047 ± 0.011 | 0.2212 ± 0.014 | 0.2095 ± 0.009 |

TABLE 21

The quantities of cannabinoids (as % of resin and mg/g of plant) in the extracts isolated, before and after winterization.

| Strains | Runs | Cannabinoid in resin before winterization | | | | Cannabinoid in resin after winterization | | | |
|---|---|---|---|---|---|---|---|---|---|
| | | CBD (%) | CBD (mg/g) | $\Delta^9$-THC (%) | $\Delta^9$-THC (mg/g) | CBD (%) | CBD (mg/g) | $\Delta^9$-THC (%) | $\Delta^9$-THC (mg/g) |
| Variety 1 (THC: 7.18/CBD: 8.6) | 1<br>2<br>3 | n.d. | n.d. | n.d. | n.d. | n.d. | n.d. | n.d. | n.d. |
| Variety 2[b] (THC: 0/CBD: 9) | 1<br>2[a]<br>3[a] | n.d. | n.d. | | | 37.6 ± 4.1 | 67.1 ± 7.1 | 1.9 ± 0.1 | 3.5 ± 0.2 |
| Variety 3[b] (THC: 18.6/CBD: 0) | 1<br>2[a]<br>3[a] | | | n.d. | n.d. | | | 49.8 ± 0.8 | 119.0 ± 1.4 | n.d. = not determined;
samples were used up before re-analysis with internal standard was performed.
[a]Average calculations based on runs 2 and 3 only.

Summary of results: Extracting and decarboxylating 1 gram scale batch of *cannabis* was successful.

Experiment 7: Larger Scale MAE (~3.75 g Batch; Before Maceration) Using the Modified Conditions 1. Dried plant material was weighed (~3.75 g per batch) and macerated using a laboratory blender at 18,000 rpm for 4 secs.
2. Crushed plant material was re-weighed and transferred to 3×20 mL microwave vials along with stir bars (~1.2 g of plant fibre per vial)
3. 95%-100% Ethanol (12 mL) was added to the vial which was then sealed and subjected to the microwave conditions below:
   Temperature=150° C.; run time=30 mins; pre-stirring=30 sec; stir rate=900 rpm; absorption=Normal
   Note: Time for decarboxylation was increased to 30 mins since analysis revealed that decarboxylation was incomplete at that scale
4. The 3×20 mL vials were combined after decarboxylation and the suspension was filtered and the filtrate and plant fibre collected separately
5. Filtrate was then concentrated at 35° C., then transferred to a 20 mL vial using ethanol and again concentrated at 35° C., weighed and stored in the refrigerator
6. Decarboxylations were performed in duplicate The results are shown in Table 22 below.

TABLE 22

| Strain | Runs | Amount of plant before maceration (g) | Amount of plant after maceration (g) | Extract isolated (g) | Average Extract isolated (g) ± SD |
|---|---|---|---|---|---|
| Variety 1 (THC: 7.18/CBD: 8.6) | 1<br>2 | 3.7922<br>3.7228 | 3.6268<br>3.5800 | 0.9967<br>0.8906 | 0.9437 ± 0.075 |
| Variety 2 (THC: 0/CBD: 9) | 1 | —[b] | 1.2427 | —[c] | —[c] |
| Variety 3 (THC: 18.6/CBD: 0) | 1<br>2 | 3.7100<br>3.8012 | 3.5978<br>3.6035 | 1.0658<br>1.2486 | 1.1572 ± 0.1293 |

[b]Plant fibre is supplied as pulverized buds. Size was appropriate, therefore no further maceration was done.
[c]Desired temperature of 150° C. could not be achieved due to pressure build-up.

Summary of results: From the results above, it can be concluded that larger scale microwave assisted extraction was successful, at 3-4 grams scale. This method can be scaled up into multi-gram and larger scales with appropriate adjustments to conditions.

Experiment 8: Large Scale Microwave-Assisted Extractions with Ethanol (MAE)

(A) General Procedure (~3.75 q Batch; Before Maceration):
1. Dried plant material was weighed and macerated using a laboratory blender at 18,000 rpm for 4 secs
2. Crushed plant material was re-weighed and transferred to 3×20 mL microwave vials along with stir bars (~1.2 g of plant fibre per vial)
3. 95%-100% Ethanol (12 mL) was added to the vial which was then sealed and subjected to the microwave conditions below:
Temperature=150° C.; run time=30 mins; pre-stirring=30 sec; stir rate=900 rpm; absorption=Normal
Note: Time for decarboxylation was increased to 30 mins since analysis revealed that decarboxylation was incomplete at that scale
4. All 20 mL vials were combined after decarboxylation and the suspension was filtered and the filtrate and plant fibre collected separately (first batch) 5. Filtrate was then concentrated at 35° C., then transferred to a 20 mL vial using ethanol and again concentrated at 35° C., weighed and stored in the refrigerator 6. Decarboxylations were performed in duplicate Winterization Procedure:
1. Same as previously described

TABLE 23

The quantities of cannabis plants used and the amounts of extract obtained before and after winterization.

| Strain | Runs | Plant before maceration (g) | Plant after maceration (g) | Extract isolated before winterization (g) | | Extract isolated after winterization (g) | |
|---|---|---|---|---|---|---|---|
| Variety 1 (THC: 7.18/CBD: 8.6) | 1[a] 2 | 3.7575 ± 0.049 | 3.6034 ± 0.033 | 0.9967 0.8906 | 0.9437 ± 0.075 | 0.7794 | |
| Variety 2 (THC: 0/CBD: 9) | 1 | 1.2427 | b | n.d. | n.d | n.d | n.d |
| Variety 3 (THC: 18.6/CBD: 0) | 1 2 | 3.7556 ± 0.064 | 3.6007 ± 0.004 | 1.0618 1.2468 | 1.1543 ± 0.131 | 0.7984 0.9961 | 0.8973 ± 0.140 | n.d. = not determined. Desired temperature of 150° C. could not be achieved due to pressure build-up; nothing further was done with buds.
[a]No winterization was performed on run 1; winterization done on run 2 only.
[b]Plant fibre is supplied as pulverized buds. Size was appropriate, therefore no further maceration was done.

TABLE 24

The quantities of cannabinoids (as % of resin and mg/g of plant) in the extracts isolated, before and after winterization.

| Strains | Runs | Cannabinoid in resin before winterization | | | | Cannabinoid in resin after winterization | | | |
|---|---|---|---|---|---|---|---|---|---|
| | | CBD (%) | CBD (mg/g) | $\Delta^9$-THC (%) | $\Delta^9$-THC (mg/g) | CBD (%) | CBD (mg/g) | $\Delta^9$-THC (%) | $\Delta^9$-THC (mg/g) |
| Variety 1 (THC: 7.18/CBD: 8.6) | 1 2[a] | n.d. | n.d. | n.d. | n.d. | 39.0 ± 2.2 | 84.9 ± 4.7 | 30.3 ± 1.4 | 66.1 ± 3.0 |
| Variety 3 (THC: 18.6/CBD: 0) | 1 2 | | | 68.6 ± 8.4 | 219.0 ± 2.7 | | | 61.1 ± 4.6 | 153.2 ± 35.0 | n.d. = not determined; samples were used up before re-analysis with internal standard was performed.
[a]Calculations based on run 2 only.

(B) General Procedure (~7.5 g Batch; Before Maceration):
  1. Dried plant material was weighed and macerated using a laboratory blender at 18,000 rpm for 10 secs
  2. Crushed plant material was re-weighed and transferred to 6×20 mL microwave vials along with stir bars (~1.2 g of plant fibre per vial)
  3. See steps 3-6 in (A) above
Winterization Procedure:
  1. Same as previously described 3. For ~4.0 g batch, see steps 3-5 in (A) above
4. For ~7.0 g batch, see steps 3-5 in (A) above
Winterization Procedure:
  1. Same as previously described

TABLE 25

The quantities of Variety 1 (THC: 7.18/CBD: 8.6) used and the amounts of extract obtained before and after winterization.

| Runs | Amount of plant before maceration (g) | Amount of plant after maceration (g) | Extract isolated before winterization (g) | Extract isolated after winterization (g) |
|---|---|---|---|---|
| 1 | 7.5361 | 3.6156 ± 0.002 | 1.0154 ± 0.064 | 0.8115 ± 0.030 |
| 2 | | | | |
| 3 | 7.5063 | 3.6640 ± 0.026 | 0.9327 ± 0.014 | 0.8247 ± 0.022 |
| 4 | | | | |

TABLE 26

The quantities of cannabinoids (as % of resin and mg/g of plant) in the Variety 1 extract isolated, before and after winterization.

| | Cannabinoid in resin before winterization | | | | Cannabinoid in resin after winterization | | | |
|---|---|---|---|---|---|---|---|---|
| Runs | CBD (%) | CBD (mg/g) | $\Delta^9$-THC (%) | $\Delta^9$-THC (mg/g) | CBD (%) | CBD (mg/g) | $\Delta^9$-THC (%) | $\Delta^9$-THC (mg/g) |
| 1 | 40.6 ± 3.9 | 113.7 ± 3.7 | 31.1 ± 2.0 | 87.3 ± 0.1 | 31.6 ± 5.5 | 70.8 ± 9.7 | 23.1 ± 4.1 | 51.6 ± 7.3 |
| 2 | | | | | | | | |
| 3 | 29.2 ± 0.1 | 74.3 ± 0.9 | 20.9 ± 1.0 | 53.3 ± 3.0 | 44.0 ± 2.9 | 99.0 ± 4.7 | 31.3 ± 0.7 | 70.3 ± 0.2 |
| 4 | | | | | | | | |

TABLE 27

The quantity of Variety 1 plant (THC: 7.18/CBD: 8.6) used and the amount of extract obtained before and after winterization.

| Runs | Amount of plant before maceration (g) | Amount of plant after maceration (g) | Extract isolated before winterization (g) | Extract isolated after winterization (g) |
|---|---|---|---|---|
| 1 | 4.0325 | 3.8199 | 0.8889 | 0.7358 |
| 2 | 7.1293 | 6.8717 | 1.5244 | 1.4101 |

(C) General Procedure (~4.0 and 7.0 q Batches; Before Maceration):
  1. Dried plant material was weighed and macerated using a laboratory blender at 18,000 rpm for 10 secs
  2. Crushed plant material was re-weighed and transferred to 20 mL microwave vials along with stir bars (~1.2 g of plant fibre per vial)

TABLE 28

The quantities of cannabinoids (as % of resin and mg/g of plant) in the Variety 1 extract isolated, before and after winterization.

| | Cannabinoid in resin before winterization | | | | Cannabinoid in resin after winterization | | | |
|---|---|---|---|---|---|---|---|---|
| Runs | CBD (%) | CBD (mg/g) | $\Delta^9$-THC (%) | $\Delta^9$-THC (mg/g) | CBD (%) | CBD (mg/g) | $\Delta^9$-THC (%) | $\Delta^9$-THC (mg/g) |
| 1 | 30.2 ± 0.0 | 70.3 ± 0.1 | 27.1 ± 0.4 | 63.0 ± 0.0 | 38.4 ± 6.1 | 73.9 ± 11.8 | 32.1 ± 7.5 | 61.8 ± 14.4 |
| 2 | 33.6 ± 2.9 | 74.5 ± 6.5 | 28.9 ± 3.2 | 64.2 ± 7.1 | 42.5 ± 0.5 | 87.2 ± 1.1 | 37.0 ± 2.9 | 75.9 ± 5.9 |

Summary of results: Extracting and decarboxylating 3.75 gram scale batch of *cannabis* was successful.

Experiment 9: Larger Scale Microwave-Assisted Extractions with Ethanol (MAE) and Winterization 1. Dried plant material was weighed (~7.5 g per batch) and macerated using a laboratory blender at 18,000 rpm for 10 secs
2. Crushed plant material was re-weighed and transferred to 6×20 mL microwave vials along with stir bars (~1.2 g of plant fibre per vial)
3. 95%-100% Ethanol (12 mL) was added to the vial which was then sealed and subjected to the microwave conditions below:
   Temperature=150° C.; run time=30 mins; pre-stirring=30 sec; stir rate=900 rpm; absorption=Normal
4. The 3×20 mL vials were combined after decarboxylation and the suspension was filtered and the filtrate and plant fibre collected separately
5. Filtrate was then concentrated at 35° C., then transferred to a 20 mL vial using ethanol and again concentrated at 35° C., weighed and stored in the refrigerator
6. Resin was dissolved in ethanol (10 mL/g)
7. Vials containing extract solution were cooled to −75° C. using a dry ice/acetone bath for 4 hrs
8. Solution was filtered with a pre-weighed syringe filter in 20 mL vials Filter specifications: Millex®-GV (sterile), Low Protein Binding Durapore® (PVDF) Membrane, 0.22 pm pore size, 33 mm diameter
9. Filter was washed with ethanol that had been cooled for 5 mins at −75° C. using a dry ice/acetone bath
10. Filtrate was concentrated at 35° C. and vacuum dried for 2 days at 40° C. (via water bath), then extract was weighed
11. Syringe filter was weighed after 2-3 days drying in the fumehood The results are shown in Table 29 below.

TABLE 29

| Strain | Runs | Amount of plant before maceration (g) | Amount of plant after maceration (g) | Extract isolated (g) | mg of cannabinoid/g of plant (%) THC | CBD |
|---|---|---|---|---|---|---|
| Variety 1 (THC: 7.18/CBD: 8.6) | 1 | 7.5063 | 3.682 | 0.8403 | 7.0 | 10.7 |
|  | 2 |  | 3.6459 | 0.8091 | 7.7 | 12.2 |

Summary of results: 7.5 g large scale batch of *cannabis* extraction and decarboxylation was successful. These experiments demonstrate that the methods of the disclosure consistently extract and decarboxylate cannabinoids and can be used on a commercial scale.

Experiment 10: Winterization

Winterization is a procedure typically used to remove waxes and other partially soluble materials at 0±10° C. temperature range. This process may not be applicable, if there are no waxes present in the extract, or such hydrophobic molecules are broken down, and would be solidify at the ice-bath or below-zero temperatures.

Experiment 10A

To remove waxes, the solutions of extract which had been stored in the refrigerator (−5° C.) for 1-3 weeks were manipulated as follows:
1. Solution was filtered using a syringe filter in 20 mL vials
   Filter specifications: Millex®-GV (sterile)
   Low Protein Binding Durapore® (PVDF) Membrane
   0.22 pm pore size
   13 m diameter
2. Filtrate was concentrated at 35° C. and vacuum dried for 3 days at 40° C. (via water bath)
3. Extracts were then re-weighed Experiment 10l3

1. Resin was dissolved in 95%-100% ethanol (10 mL/g) and heated at 40° C. for 5 mins in a water bath
2. Vial containing extract solution was cooled to −75° C. using a dry ice/acetone bath for 3-3.75 hrs
3. Solution was filtered with a pre-weighed syringe filter in 20 mL vials (see above for filter specifications); filter was washed with ethanol that had been cooled for 5 mins at −75° C. using a dry ice/acetone bath
4. Filtrate was concentrated at 35° C. and extract was weighed
5. Syringe filter was weighed after 2-3 days drying in the fumehood The results are shown in Tables 30a and b below.

TABLE 30a

Amount of extract isolated before and after winterization methods

| Strain | Runs | Before 1$^{st}$ winterization (g) | After 1$^{st}$ winterization and drying (g) | After 2$^{nd}$ winterization and drying (g) |
|---|---|---|---|---|
| Variety 1 (THC: 7.18/CBD: 8.6) | 1 | 0.2044 | 0.2111 | 0.2031 |
|  | 2 | 0.2184 | 0.2345 | 0.1964 |
|  | 3 | 0.2088 | 0.1981 | 0.1891 |
| Variety 2 (THC: 0/CBD: 9) | 1 | 0.1624 | 0.1677 | 0.1580 |
|  | 2 | 0.1721 | 0.1622 | 0.1508 |
|  | 3 | 0.1617 | 0.1677 | 0.1536 |
| Variety 3 (THC: 18.6/CBD: 0) | 1 | 0.2225 | 0.2088 | 0.1996 |
|  | 2 | 0.2068 | 0.2221 | 0.2145 |
|  | 3 | 0.2343 | 0.2243 | 0.2145 |

TABLE 30b

Average extract isolated before and after winterization methods

| Strain | Runs | Before 1st winterization (g) | After 1st winterization and drying (g) | After 2nd winterization and drying (g) |
|---|---|---|---|---|
| Variety 1 (THC: 7.18/CBD: 8.6) | 1 2 3 | 0.2105 ± 0.007 | 0.2146 ± 0.018 | 0.1962 ± 0.007 |
| Variety 2 (THC: 0/CBD: 9) | 1 2 3 | 0.1654 ± 0.006 | 0.1659 ± 0.003 | 0.1541 ± 0.004 |
| Variety 3 (THC: 18.6/CBD: 0) | 1 2 3 | 0.2212 ± 0.014 | 0.2184 ± 0.008 | 0.2095 ± 0.009 |

Tables 31a and b below show the amount of cannabinoid (in milligrams) in the extract per gram of plant material isolated before and after winterization methods TABLE 31a Amount of cannabinoid (in milligrams) in the extract per gram pf plant material

| Strains | Runs | Before 1$^{st}$ winterization (mg/g) CBD | Before 1$^{st}$ winterization (mg/g) $\Delta^9$-THC | 1$^{st}$ winterization (mg/g) CBD | 1$^{st}$ winterization (mg/g) $\Delta^9$-THC | 2$^{nd}$ winterization (mg/g) CBD | 2$^{nd}$ winterization (mg/g) $\Delta^9$-THC |
|---|---|---|---|---|---|---|---|
| Variety 1 | 1 | 92.9 | 65.1 | 98.3 | 76.2 | 157.4 | 109.0 |
| (THC: 7.18/ | 2 | 114.9 | 82.3 | 114.3 | 91.5 | 124.7 | 93.7 |
| CBD: 8.6) | 3 | 115.5 | 85.7 | 113.7 | 93.8 | 184.5 | 138.1 |
| Variety 2 | 1 | 200.5 | | 113.7 | | 149.7 | |
| (THC: 0/ | 2 | 211.6 | | 109.5 | | 147.3 | |
| CBD: 9) | 3 | 146.9 | | 131.2 | | 161.9 | |
| Variety 3 | 1 | | 406.1 | | 207.7 | | 235.4 |
| (THC: 18.6/ | 2 | | 185.6 | | 274.8 | | 236.2 |
| CBD: 0) | 3 | | 232.9 | | 301.0 | | 283.4 |

TABLE 31b

Average cannabinoid (in milligrams) in the extract per gram pf plant material

| Strains | Runs | Before 1$^{st}$ winterization (mg/g) CBD | Before 1$^{st}$ winterization (mg/g) $\Delta^9$-THC | 1$^{st}$ winterization (mg/g) CBD | 1$^{st}$ winterization (mg/g) $\Delta^9$-THC | 2$^{nd}$ winterization (mg/g) CBD | 2$^{nd}$ winterization (mg/g) $\Delta^9$-THC |
|---|---|---|---|---|---|---|---|
| Variety 1 (THC: 7.18/CBD: 8.6) | 1 2 3 | 107.8 ± 12.9 | 77.7 ± 11.0 | 108.8 ± 9.1 | 87.2 ± 9.6 | 155.5 ± 29.9 | 113.6 ± 22.6 |
| Variety 2 (THC: 0/CBD: 9) | 1 2 3 | 186.3 ± 34.6 | | 118.1 ± 11.5 | | 153.0 ± 7.8 | |
| Variety 3 (THC: 18.6/CBD: 0) | 1 2 3 | | 274.9 ± 116.1 | | 261.2 ± 48.1 | | 251.7 ± 27.5 |

Summary of results: Winterization of extracts was successful in removing waxes from the extract.

Experiment 11: Chemistry of Medicinal *Cannabis* Before and After Decarboxylation Methodology
Extraction:

Dried plant material (1 g) was weighed and transferred to a mortar and was macerated using a pestle. The crused plant material was then transferred into a 10 mL vessel and was subjected to supercritical fluid extraction (SFE), with supercritical $CO_2$ as solvent A and ethanol as solvent B. The photodiode array detector was set to monitor wavelengths in the range of 200-600 nm and the back pressure regulator was set to 12 MPa. The SFE conditions used were: flow rate=10 mL/min ($CO_2$ and slave pumps) and 1 mL/min (make-up pump); temperature=25° C.; gradient: 100% A–50% A (0.1-25 mins), 100% B (25-26 mins) and 100% A (26-30 mins). Once the method was completed, all fractions were combined and concentrated to dryness under reduced pressure (at 25° C.) to afford 0.28 g of a green sticky resin. This was used for further work-up and analyses.

Activation:

Activation of phytocannabinoids was conducted by subjecting *cannabis* extract to heat using microwaves. A 5 mL-size microwave vial was charged with *cannabis* extract (27.72 mg) dissolved in ethanol (2 mL). The vial was sealed and was subjected to heat for 10 min at 150° C. in a pressure vessel to afford a green sticky extract. This was concentrated to dryness at 35° C. to obtain the activated *cannabis* extract as a resin (21.2 mg).

Figure 28A:
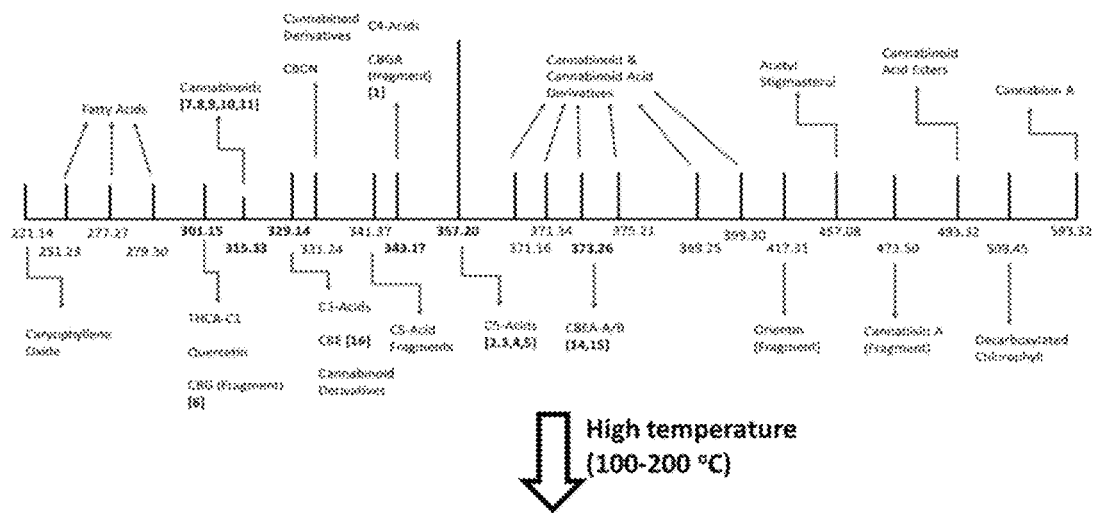
Figure 28B:
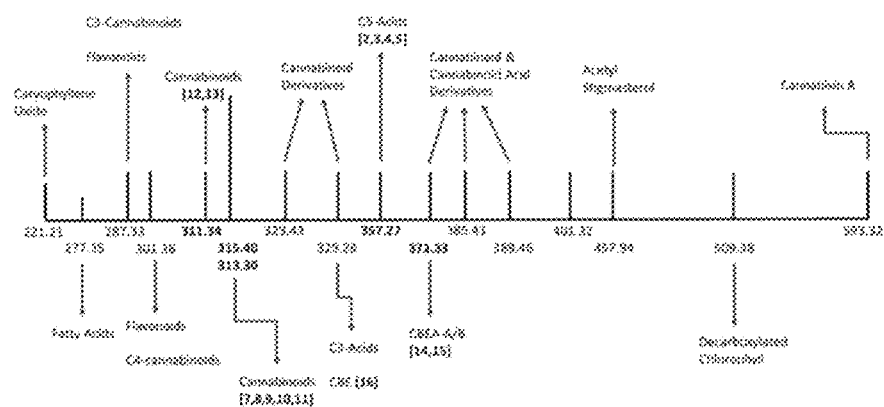

FIGS. 28A and 28B show the overview of select signals as seen in the mass spectra before (A) and after (B) decarboxylation of *cannabis* extract, as well as their corresponding compound classes. Bolded signals are compounds identified in the cannabinoid biosynthetic pathway.

Table 32.

Potential changes in chemical composition after decarboxylation of strain I *cannabis* extract. Left column indicates the potential compounds that were present in *cannabis* extract obtained through a supercritical fluid extraction (SFE), but not in the decarboxylated resin. This extract was then subjected to heating conditions using microwave technology, and the right column shows the new chemicals that were identified, which were not present in the *cannabis* extract prior to employing microwave technology described in this disclosure.

TABLE 32

| Compounds Lost Upon Activation | New Compounds Found Upon Activation |
|---|---|
| Roughanic acid (Fatty acid) | Kaempferol (Flavonol) |
| α-Linolenic acid (Fatty acid) | Luteolin (Flavonol) |
| Quercetin (Flavonoid) | 4,7-Dimethoxy-1,2,5-trihydroxyphenanthrene (Non-cannabinoid) |
| 4,5-Dihydroxy-2,3,6-trimethoxy-9,10-dihydrophenanthrene (Non-cannabinoid) | 5-Methyl-4-pentyl-2,6,2-trihydroxybiphenyl (Non-cannabinoid) |
| $\Delta^9$-Tetrahydrocannabiorcolic acid ($C_1$-Cannabinoid Acid) | 5-Methyl-4-pentylbiphenyl-2,2,6-triol (Non-cannabinoid) |
| Cannabigerol ($C_5$-Neutral Cannabinoid) | |
| Cannabichromanon (Neutral Cannabinoid) | Cannabichromevarin ($C_3$-Neutral Cannabinoid) |

TABLE 32-continued

| Compounds Lost Upon Activation | New Compounds Found Upon Activation |
|---|---|
| Cannabigerovarinic acid ($C_5$-Cannabinoid Acid) | Cannabicyclovarin ($C_3$-Neutral Cannabinoid) |
| 6,7-cis/trans-Epoxycannabigerol (Cannabinoid Derivative) | Cannabidivarin ($C_3$-Neutral Cannabinoid) |
| 7-Hydroxycannabichromane (Cannabinoid Derivative) | $\Delta^7$-cis-iso-Tetrahydrocannabivarin ($C_3$-Neutral Cannabinoid) |
| $C_4$-Tetrahydrocannabinolic acid ($C_4$-Cannabinoid Acid) | $\Delta^9$-tetrahydrocannabivarin ($C_3$-Neutral Cannabinoid) |
| Cannabitriol (Neutral Cannabinoid) | Chrysoeriol (Flavone) |
| Cannabiripsol (Neutral Cannabinoid) | $C_4$-Cannabidiol ($C_4$-Neutral Cannabinoid) |
| Cannabigerolic Acid ($C_5$-Cannabinoid Acid) | $C_4$-Tetrahydrocannabinol ($C_4$-Neutral Cannabinoid) |
| 7R-Cannabicoumaronic Acid (Cannabinoid Acid) | Cannabifuran (Neutral Cannabinoid) |
| Tetrahydrocannabinolic acid-8-one (Cannabinoid Acid Derivative) | Cannabinol ($C_5$-Neutral Cannabinoid) |
| 5-Acetoxy-6-geranyl-3-n-pentyl-1,4-benzoquinone (Non-cannabinoid) | Cannabinodiol ($C_5$-Neutral Cannabinoid) |
| 4-Acetoxycannabichromene (Cannabinoid Derivative) | 10-oxo-$\Delta^{6a}$-tetrahydrocannabinol (Cannabinoid Derivative) |
| Cannabielsoic Acid-$\alpha/\beta$ (Cannabinoid Acid) | 7R-Cannabicourmarone (Neutral Cannabinoid) |
| 6,7-trans/cis-Epoxycannabigerolic acid (Cannabinoid Acid Derivative) | Cannabichromanone-D (Neutral Cannabinoid) |
| $\Delta^9$-Tetrahydrocannabinolic acid + $C_2H_2O$ (Cannabinoid Acid Derivative) | Cannabidiol Monoethylether (Cannabinoid Derivative) |
| Orientin (Flavone) | Cannabielsoic Acid-A/B (Cannabinoid Acid) |
| 4-Terpenyl-$\Delta^9$-Tetrahydrocannabinolate (Cannabinoid Acid Ester) | Sesquicannabigerol (Cannabinoid Derivative) |
| $\alpha$-Terpenyl-$\Delta^9$-Tetrahydrocannabinolate (Cannabinoid Acid Ester) | |
| Bornyl/epi-bornyl-$\Delta^9$-Tetrahydrocannabinolate (Cannabinoid Acid Ester) | |
| $\alpha/\beta$-Fenchyl $\Delta^9$-Tetrahydrocannabinolate (Cannabinoid Acid Ester) | |

Closed system, microwave extraction provided the simultaneous extraction and decarboxylation of the cannabinoids. In the native *cannabis* extract, 63 compounds could be observed (FIG. 28A), and in the decarboxylated *cannabis* extract, there could be up to 22 new compounds (Table 32). Up to 26 compounds from the resin were not present in the decarboxylated *cannabis* resin, but were present in the *cannabis* resin prior to decarboxylation step.

Experiment 12: Solvent-Free Decarboxylated *Cannabis* Resin

General Procedure

To remove the solvent from the decarboxylated resin, the following procedures are used:

distillers or rotary evaporators are used to evaporate solvents employed in extraction and decarboxylation process, concentrate and obtain solvent-free decarboxylated resin. During the evaporation of solvent, a higher temperature than ambient temperature is used to facilitate faster evaporation of the solvent. In addition, a vacuum may be used to facilitate removal of solvent at lower pressure than the atmospheric pressure. In general, such processes are well established and known to those skilled in the art.

The resulting decarboxylated *cannabis* resin may comprise less than 5% solvent, or the resin can be solvent-free.

Where aspects or embodiments of the invention are described in terms of a Markush group or other grouping of alternatives, the present invention encompasses not only the entire group listed as a whole, but each member of the group individually and all possible subgroups of the main group, but also the main group absent one or more of the group members. The present invention also envisages the explicit exclusion of one or more of any of the group members in the claimed invention.

Numerical data may be presented herein in a range format. It is to be understood that such a range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, a numerical range of about 1 to about 4.5 should be interpreted to include not only the explicitly recited limits of 1 to about 4.5, but also to include individual numerals such as 2, 3, 4, and sub-ranges such as 1 to 3, 2 to 4 etc. The same principle applies to ranges reciting only one numerical value, such as "less than about 4.5," which should be interpreted to include all of the above-recited values and ranges. Further, such an interpretation should apply regardless of the breadth of the range or the characteristic being described.

While the foregoing disclosure has been described in some detail for purposes of clarity and understanding, it will be appreciated by one skilled in the art, from a reading of the disclosure that various changes in form and detail can be made without departing from the true scope of the disclosure in the appended claims.

All publications, patents, and patent applications are herein incorporated by reference in their entirety to the same extent as if each individual publication, patent or patent application was specifically and individually indicated to be incorporated by reference in its entirety.

What is claimed is:

1. A method of extracting and decarboxylating cannabinoids from *cannabis*, the method comprising:
    (i) extracting cannabinoids by contacting the *cannabis* with a solvent, thereby forming a *cannabis* extract,
    (ii) decarboxylating the cannabinoids in the *cannabis* extract by subjecting the *cannabis* extract to microwaves at a temperature of about 100° C.-200° C. in a sealed container for a time period sufficient to form the corresponding decarboxylated cannabinoids in the *cannabis* extract, and (iii) removing the solvent from the *cannabis* extract, thereby producing a *cannabis* resin;

wherein the decarboxylated cannabinoids in the *cannabis* resin are then subjected to winterization, and wherein the solvent is selected from the group consisting of 80%-100% ethanol, ethylene glycol, isopropanol, and combinations thereof.

2. The method of claim 1, wherein the *cannabis* remains in contact with the solvent during the decarboxylating step.

3. The method of claim 2, wherein the extracting and decarboxylating occur concurrently.

4. The method of claim 1, wherein before the step of extracting, the *cannabis* is broken down to produce *cannabis* of a size and form suitable for extraction.

5. The method of claim 1, wherein the time period is about 15-75 minutes and wherein the temperature is about 130° C. to about 180° C.

6. The method of claim 1, wherein the microwaves have a frequency of about 2.45 GHz.

7. The method of claim 1, wherein the decarboxylating step occurs under a pressure of about 2-22 bar.

8. The method of claim 1, wherein the *cannabis* is a part selected from the group consisting of a trichome, a *cannabis* female inflorescence, a flower bract, a *cannabis* stalk, a *cannabis* leaf, and combinations thereof.

9. The method of claim 1, wherein the extracted and decarboxylated cannabinoids are recovered in the form of isolated compounds.

10. The method of claim 4, wherein prior to the step where the *cannabis* is broken down, the *cannabis* is dried.

* * * * *